US006569148B2

(12) United States Patent
Bagaoisan et al.

(10) Patent No.: US 6,569,148 B2
(45) Date of Patent: May 27, 2003

(54) METHODS FOR EMBOLI CONTAINMENT

(75) Inventors: Celso J. Bagaoisan, Union City, CA (US); Jefferey C. Bleam, Boulder Creek, CA (US); Ketan P. Muni, San Jose, CA (US); Gholam RezaZadno Azizi, Fremont, CA (US)

(73) Assignee: MedTronic Ave, Inc., Santa Rosa, CA (US)

( * ) Notice: Subject to any disclaimer, the term of this patent is extended or adjusted under 35 U.S.C. 154(b) by 0 days.

(21) Appl. No.: 09/769,775

(22) Filed: Jan. 25, 2001

(65) Prior Publication Data

US 2002/0029031 A1 Mar. 7, 2002

Related U.S. Application Data

(63) Continuation of application No. 09/314,054, filed on May 18, 1999, which is a continuation of application No. 08/812,570, filed on Mar. 6, 1997, now Pat. No. 6,022,336, which is a continuation-in-part of application No. 08/650,464, filed on May 20, 1996, now abandoned.

(51) Int. Cl.[7] ............................................... A61M 31/00
(52) U.S. Cl. .................... 604/509; 604/507; 604/101.04
(58) Field of Search ........................... 606/1, 127, 167, 606/159, 180, 194; 604/22, 96–104, 500, 506, 507–510

(56) References Cited

U.S. PATENT DOCUMENTS

| | | |
|---|---|---|
| 3,045,677 A | 7/1962 | Wallace |
| 3,144,868 A | 8/1964 | Jascalevich ................ 128/350 |
| 4,024,873 A | 5/1977 | Antoshkiw et al. |
| 4,276,874 A | 7/1981 | Wolvek et al. .............. 128/1 D |
| 4,295,464 A | 10/1981 | Shihata |
| 4,445,892 A | 5/1984 | Hussein et al. ............. 604/101 |
| 4,468,216 A | 8/1984 | Muto ........................... 604/43 |
| 4,511,354 A | 4/1985 | Sterling ....................... 604/98 |
| 4,573,966 A | 3/1986 | Weikl et al. ................. 604/53 |
| 4,610,662 A | 9/1986 | Weikl et al. ................. 604/53 |
| 4,636,195 A | 1/1987 | Wolinsky ..................... 604/53 |
| 4,655,746 A | 4/1987 | Daniels et al. ............... 604/53 |
| 4,692,139 A | 9/1987 | Stiles |
| 4,696,668 A | 9/1987 | Wilcox |
| 4,705,507 A | 11/1987 | Boyles ....................... 604/101 |
| 4,714,460 A | 12/1987 | Calderon ..................... 604/28 |

(List continued on next page.)

FOREIGN PATENT DOCUMENTS

| | | |
|---|---|---|
| DE | 38 04 849 A1 | 2/1987 |
| DE | 3804849 A1 | 9/1988 |
| EP | 0 402 467 | 10/1989 |

(List continued on next page.)

OTHER PUBLICATIONS

"Carotid Endarterectomy" Hershy/Calman, Atlas of Vascular Surgery, pp. 311–318, 1973.

(List continued on next page.)

*Primary Examiner*—Brian L. Casler
*Assistant Examiner*—Jennifer Maynord
(74) *Attorney, Agent, or Firm*—Knobbe, Martens, Olson & Bear LLP

(57) ABSTRACT

A multi-catheter emboli containment system is disclosed which is adapted to provide at least one pair of optimized paths for irrigation and aspiration fluid flow. Through careful design of the cross-sectional area of these paths, the present system is able to be compactly utilized in even the smaller size blood vessels. The catheter system itself is provided with occlusive devices to form an emboli containment chamber in which irrigation and aspiration occur. The catheter system of the present invention provides an improved emboli containment and removal system which can be utilized in a wide range of vessel diameters. The system is easy to use and can quickly and efficiently evacuate the containment chamber.

12 Claims, 18 Drawing Sheets

U.S. PATENT DOCUMENTS

| | | | |
|---|---|---|---|
| 4,748,982 A | 6/1988 | Horzewski et al. | 128/344 |
| 4,763,654 A | 8/1988 | Jang | |
| 4,781,677 A | 11/1988 | Wilcox | |
| 4,790,812 A | 12/1988 | Hawkins, Jr. et al. | 604/22 |
| 4,790,813 A | 12/1988 | Kensey | 604/22 |
| 4,794,928 A | 1/1989 | Kletschka | |
| 4,824,436 A | 4/1989 | Wolinsky | 604/53 |
| 4,832,028 A | 5/1989 | Patel | 128/344 |
| 4,838,268 A | 6/1989 | Keith et al. | 128/344 |
| 4,842,579 A | 6/1989 | Shiber. | |
| 4,867,742 A | 9/1989 | Calderon | |
| 4,911,163 A | 3/1990 | Fina | 606/127 |
| 4,921,478 A | 5/1990 | Solano et al. | |
| 4,926,858 A | 5/1990 | Gifford, III et al. | |
| 4,946,466 A | 8/1990 | Pinchuk et al. | 604/194 |
| 4,950,238 A | 8/1990 | Sullivan | 604/22 |
| 4,964,409 A | 10/1990 | Tremulis | 128/657 |
| 4,998,917 A | 3/1991 | Gaiser et al. | 604/96 |
| 5,000,743 A | 3/1991 | Patel | 606/194 |
| 5,035,686 A | 7/1991 | Crittenden et al. | 604/96 |
| 5,059,178 A | 10/1991 | Ya | 604/101 |
| 5,102,415 A | 4/1992 | Guenther et al. | |
| 5,135,484 A | 8/1992 | Wright | 604/28 |
| 5,152,277 A | 10/1992 | Honda et al. | 128/4 |
| 5,163,905 A | 11/1992 | Don Michael | |
| 5,163,906 A | 11/1992 | Ahmadi | 604/101 |
| 5,167,239 A | 12/1992 | Cohen et al. | 128/772 |
| 5,184,627 A | 2/1993 | de Toledo | 128/772 |
| 5,195,955 A | 3/1993 | Don Michael | 604/22 |
| 5,211,636 A | 5/1993 | Mische | 604/264 |
| 5,213,577 A | 5/1993 | Kratzer | 604/101 |
| 5,221,270 A | 6/1993 | Parker | 604/282 |
| 5,226,889 A | 7/1993 | Sheiban | 604/101 |
| 5,250,060 A | 10/1993 | Carbo et al. | 606/159 |
| 5,256,141 A | 10/1993 | Gencheff et al. | 604/53 |
| 5,279,546 A | 1/1994 | Mische et al. | 604/22 |
| 5,281,200 A | 1/1994 | Corso, Jr. et al. | 604/96 |
| 5,320,604 A | 6/1994 | Walker et al. | 604/96 |
| 5,320,605 A | 6/1994 | Sahota | 604/101 |
| 5,322,508 A | 6/1994 | Viera | 604/52 |
| 5,324,259 A | 6/1994 | Taylor et al. | 604/96 |
| 5,328,471 A | 7/1994 | Slepian | 604/101 |
| 5,342,306 A | 8/1994 | Don Michael | 604/101 |
| 5,370,608 A | 12/1994 | Sahota et al. | 604/20 |
| 5,380,284 A | 1/1995 | Don Micheal | 601/101 |
| 5,383,856 A | 1/1995 | Bersin | 604/101 |
| 5,395,311 A | 3/1995 | Andrews | 604/22 |
| 5,395,333 A | 3/1995 | Brill | 604/101 |
| 5,397,307 A | 3/1995 | Goodin | 604/96 |
| 5,403,274 A | 4/1995 | Cannon | 604/9 |
| 5,405,322 A | 4/1995 | Lennox et al. | 604/53 |
| 5,413,558 A | 5/1995 | Paradis | 604/101 |
| 5,415,635 A | 5/1995 | Bagaoisan et al. | 604/96 |
| 5,415,636 A | 5/1995 | Forman | 604/101 |
| 5,423,742 A | 6/1995 | Theron | 604/28 |
| 5,423,744 A | 6/1995 | Gencheff et al. | 604/53 |
| 5,437,638 A | 8/1995 | Bowman | 604/101 |
| 5,439,000 A | 8/1995 | Gunderson et al. | 128/664 |
| 5,439,446 A | 8/1995 | Barry | 604/96 |
| 5,449,343 A | 9/1995 | Samson et al. | 604/96 |
| 5,451,209 A | 9/1995 | Ainsworth et al. | 604/96 |
| 5,458,573 A | 10/1995 | Summers | 604/101 |
| 5,458,574 A | 10/1995 | Machold et al. | 604/101 |
| 5,460,610 A | 10/1995 | Michael | 604/101 |
| 5,462,529 A | 10/1995 | Simpson et al. | 604/101 |
| 5,464,394 A | 11/1995 | Miller et al. | |
| 5,468,239 A | 11/1995 | Tanner et al. | 606/15 |
| 5,476,450 A | 12/1995 | Ruggio | 604/93 |
| 5,478,309 A | 12/1995 | Sweezer et al. | 604/4 |
| 5,484,412 A | 1/1996 | Pierpont | 604/101 |
| 5,490,859 A | 2/1996 | Mische et al. | |
| 5,496,346 A | 3/1996 | Horzewski et al. | 606/194 |
| 5,500,180 A | 3/1996 | Anderson et al. | 264/532 |
| 5,501,694 A | 3/1996 | Ressemann et al. | |
| 5,505,700 A | 4/1996 | Leone et al. | 604/96 |
| 5,505,701 A | 4/1996 | Fernandez de Lomana | 604/99 |
| 5,505,702 A | 4/1996 | Amey | 604/101 |
| 5,514,092 A | 5/1996 | Forman et al. | 604/101 |
| 5,533,987 A | 7/1996 | Pray et al. | 604/280 |
| 5,549,626 A | 8/1996 | Miller et al. | |
| 5,567,203 A | 10/1996 | Euteneuer et al. | 604/96 |
| 5,599,307 A | 2/1997 | Bacher et al. | |
| 5,634,897 A | 6/1997 | Dance et al. | |
| 5,645,533 A | 7/1997 | Blaeser et al. | 604/164 |
| 5,662,671 A | 9/1997 | Barbut et al. | |
| 5,674,198 A | 10/1997 | Leone | |
| 5,681,336 A * | 10/1997 | Clement et al. | 606/159 |
| 5,688,234 A | 11/1997 | Frisbe | |
| 5,695,519 A | 12/1997 | Summers et al. | |
| 5,713,848 A | 2/1998 | Dubrul et al. | |
| 5,728,123 A * | 3/1998 | Lemelson et al. | 604/22 |
| 5,779,721 A | 7/1998 | Nash | 606/159 |
| 5,800,457 A | 9/1998 | Gelbfish | |
| 5,814,064 A | 9/1998 | Daniel et al. | |
| 5,823,996 A | 10/1998 | Sparks | |
| 5,833,644 A | 11/1998 | Zadno-Azizi et al. | |
| 5,833,650 A | 11/1998 | Imran | |
| 5,879,361 A | 3/1999 | Nash | 606/159 |
| 5,925,016 A | 7/1999 | Chomenky et al. | |
| 5,928,192 A | 7/1999 | Maahs | |
| 5,935,139 A | 8/1999 | Bates | |
| 5,938,672 A | 8/1999 | Nash | 606/159 |
| 5,954,745 A | 9/1999 | Gertler et al. | |
| 5,957,879 A | 9/1999 | Roberts et al. | |
| 5,993,469 A | 11/1999 | McKenzie et al. | |
| 6,022,336 A | 2/2000 | Zadno-Azizi et al. | |
| 6,048,331 A | 4/2000 | Tsugita et al. | |
| 6,051,014 A | 4/2000 | Jang | |
| 6,080,170 A * | 6/2000 | Nash et al. | 606/159 |
| 6,126,635 A | 10/2000 | Simpson et al. | |
| 6,135,991 A | 10/2000 | Muni et al. | |
| 6,152,909 A | 11/2000 | Bagaoisan et al. | |
| 6,217,548 B1 | 4/2001 | Tsugita et al. | |
| 6,287,271 B1 | 9/2001 | Dubrul et al. | |
| 6,309,399 B1 | 10/2001 | Barbut et al. | |

FOREIGN PATENT DOCUMENTS

| | | | |
|---|---|---|---|
| EP | EP 0 693 295 | 7/1995 | |
| WO | WO/89/01309 | 2/1989 | |
| WO | WO 95/09024 | 9/1994 | |
| WO | WO/96/01079 | 1/1996 | |
| WO | WO/96/01591 | 1/1996 | |
| WO | WO 96/15824 | 5/1996 | A61M/29/00 |
| WO | WO 97/44082 | 5/1997 | |
| WO | WO/97/44082 | 11/1997 | |
| WO | WO/98/26833 | 6/1998 | |
| WO | WO/98/33443 | 8/1998 | |
| WO | WO/98/38930 | 9/1998 | |

OTHER PUBLICATIONS

"Percutaneous Transluminal Angioplasty in Arteriosclerotic Internal Carotid Artery Stenosis" Bockenheimer, et al., AJNR, 4:791–792, May/Jun. 1983.

"Percutaneous Transluminal Angioplasty of the Carotid Artery" Tsai, et al., AJNR, 7:349–358, Mar./Apr. 1986.

"Practical Aspects of Percutaneous Transluminal Angioplasty of the Carotid Artery" Tsai, et al., ACTA Radiological, Supplementum 369, XIII Symposium Neuroradiologicum Stockholm, Jun. 1986.

"Transluminal Angioplasty for the Treatment of Carotid Artery Stenosis" Freitag, et al., VASA, Band 16, Heft 1, 1987.

"Feasibility of Percutaneous Transluminal Angioplasty for Carotid Artery Stenosis" Brown, et al., Journal of Neurology, Neurosurgery, and Psychiatry, 53(3): 238–243, Mar. 1990.

"Percutaneous Angioplasty of Artherosclerotic Carotid Arteries" Porta, et al., Cerebrovasc Dis., 1:265–272, 1991.

"Percutaneous Transluminal Angioplasty (PTA) of Supra–Aortic Arteries Especially the Internal Carotid Artery" Kachel, et al., Neuroradiology, 33(3): 191–194, 1991.

"Carotid Endarterectomy: The Gold Standard" Zarins, Journal of Endovascular Surgery, 2(1): pp. 10–15, Feb. 1996.

"Angiojet® System Used to Treat Stroke Victim" Possis Medical, Inc., News Release Sep. 11, 1996.

"Current and Future Treatment of Carotid Bifurcation Atherosclerotic Disease: A Perspective" Becker, Journal of Vascular and Interventional Radiology, 8(1): 3–8, Jan.–Feb. 1997.

"Percutaneous Angioplasty of Atherosclerotic and Postsurgical Stenosis of Carotid Arteries" J. Theron et al., AJNR, 6:495–500, May/Jun. 1987.

"Coronary and Perifpheral Angioplasty: Historic Perspective" Myler, et al., *II–Coronary and Peripheral Angioplasty*, Chapter 9, pp. 171–185.

"Restenosis: The Clinical Issues" Hillegass, et al.,*II–Coronary and Peripheral Angioplasty*, Chapter 22, pp. 415–435.

"The Pathology of Interventional Coronary Artery Techniques and Devices" Waller, et al., *II–Coronary and Peripheral Angioplasty*, Chapter 24, pp. 449–476.

"Perfusion Angioplasty" Kereiakes, et al., *II–Coronary and Peripheral Angioplasty*, Chapter 25, pp. 477–494.

"Angiplasty and Interventional Vascular Procedures in the Peripheral, Renal, Visceral and Extracranial Circulation" Wholey, et al., *II–Coronary and Peripheral Angioplasty*, Chapter 33, pp. 600–628.

"DCA Device" (section) and summary *III–Coronary Atherectomy*, Chapter 35, pp. 642, 657, and 658.

"Percutaneous Coronary Rotational Angioplasty with the Rotablator" Bertrand, et al., *III–Coronary Atherectomy*, Chapter 36, pp. 659, 666,and 667.

"Extraction Atherectomy" *III–Coronary Atherectomy*, Chapter 37, pp. 669, 675–677.

"Cirrus: Occulsion Balloon Micron Catheter" Micro Interventional Systems, Inc., *Advertisement*.

"Grapevine: Over–the–Wire Coaxial Lumen BalloonTipped Micro Catheter" Micro Interventional Systems, Inc.,*Advertisement*.

"Zeppelin–6.4F: Balloon–Tipped Guiding Catheter"Micro Interventional Systems, Inc., *Advertisement*.

"Zeppelin–842: Balloon Guiding Catheter Provides Flow Control During Ethanol Embolotherapy" Bell, et al. for Micro Interventional Systems, Inc., *Advertisement*.

"Zeppelin–1066: Balloon Guiding Catheter Controls Flow During Detachable Balloon Delivery"Micro Interventional Systems, Inc., *Advertisement*.

"Zeppelin–1066: Flow Control and Protection During Carotid Angioplasty" Micro Interventional Systems, Inc., *Advertisement*.

"Zeppelin–1066: Flow Control Improves Safety During CCF Embolization"Micro Interventional Systems, Inc., *Advertisement*.

"Zeppelin–1066: Provides Flow Control and Protection During Detachable Balloon Occulusion" Micro Interventional Systems, Inc., *Advertisement*.

"Zeppelin: Balloon Guiding Catheter" Micro Interventional Systems, Inc., *Advertisement*.

"New Triple Coaxial Catheter System for Carotid Angioplasty with Cerebral Protection"Theron, et al., *AJNR*, 11:869–874, Sep./Oct. 1990.

"Angiojet F105: Rapid Thromberctomy Catheter" Possis Medical, Inc., *Advertisement*, 9/95.

"Angiojet LF140: Rapid Thrombectomy Catheter" Possis Medical, Inc., *Avertisement*, 9/95.

* cited by examiner

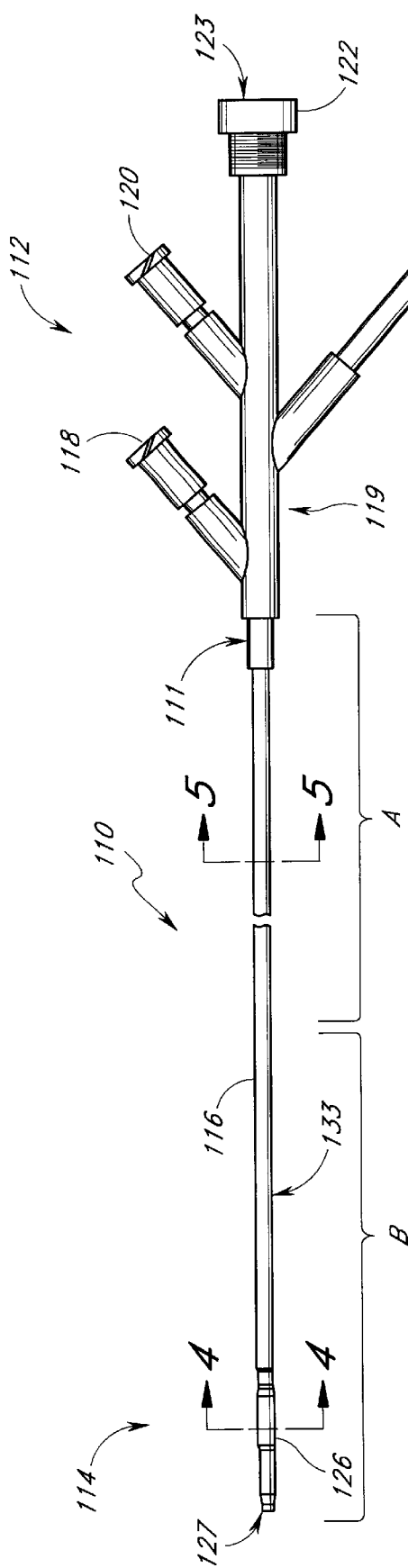
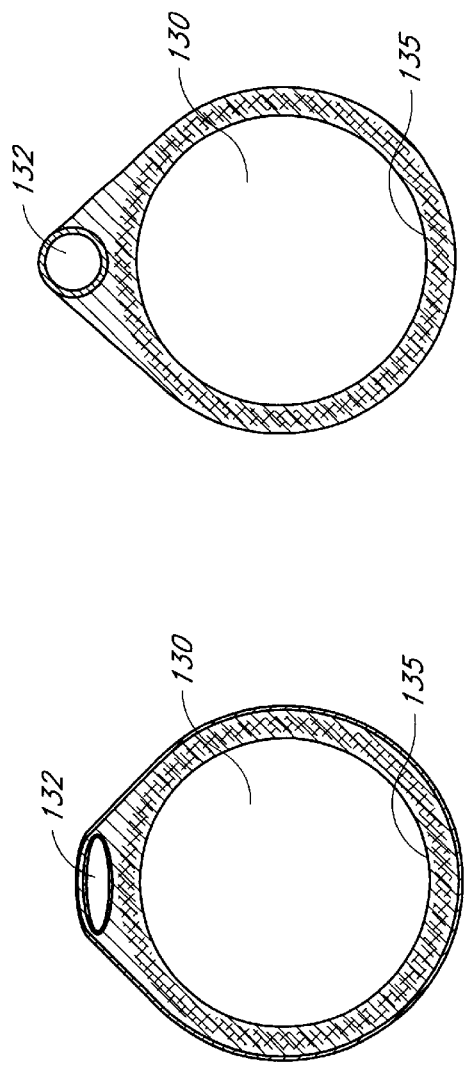
FIG. 3
FIG. 4
FIG. 5

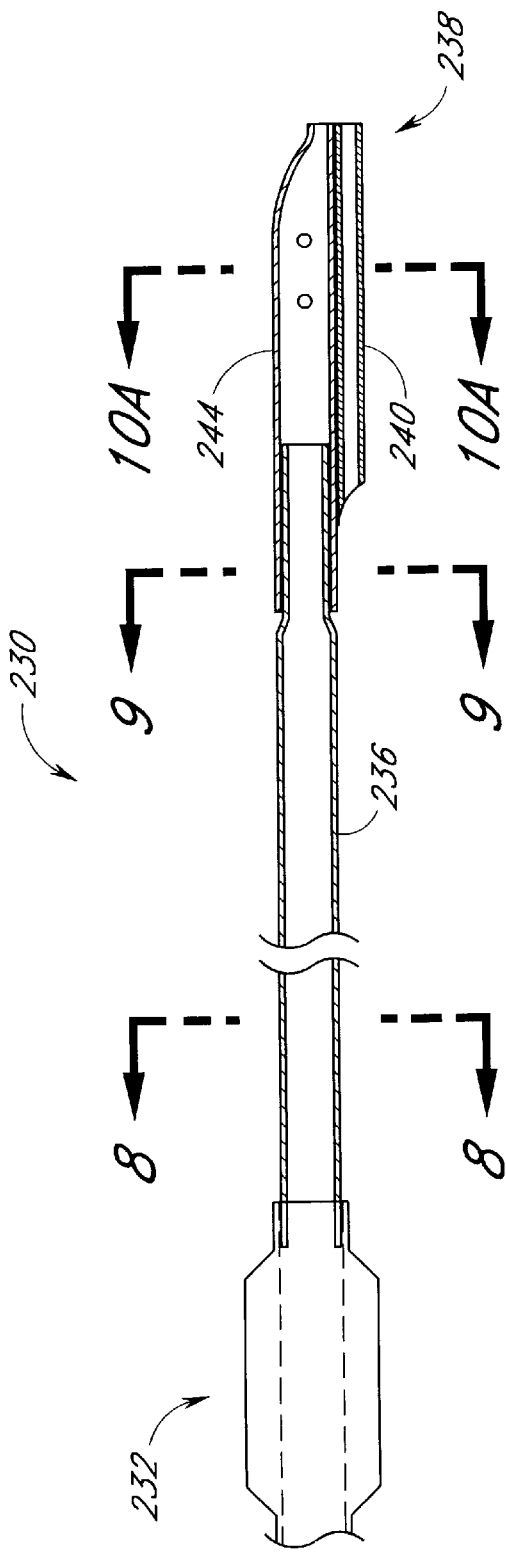
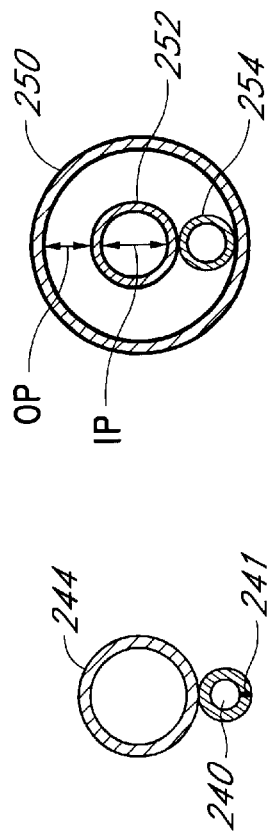
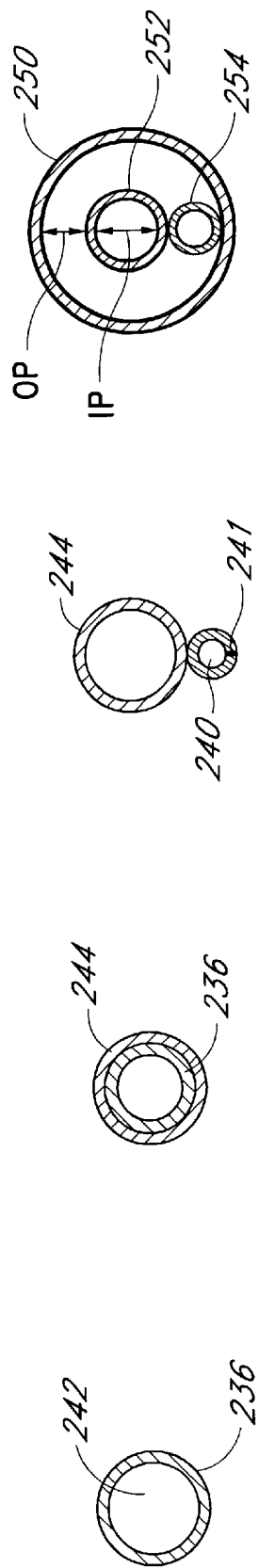
FIG. 7
FIG. 8
FIG. 9
FIG. 10A
FIG. 10B

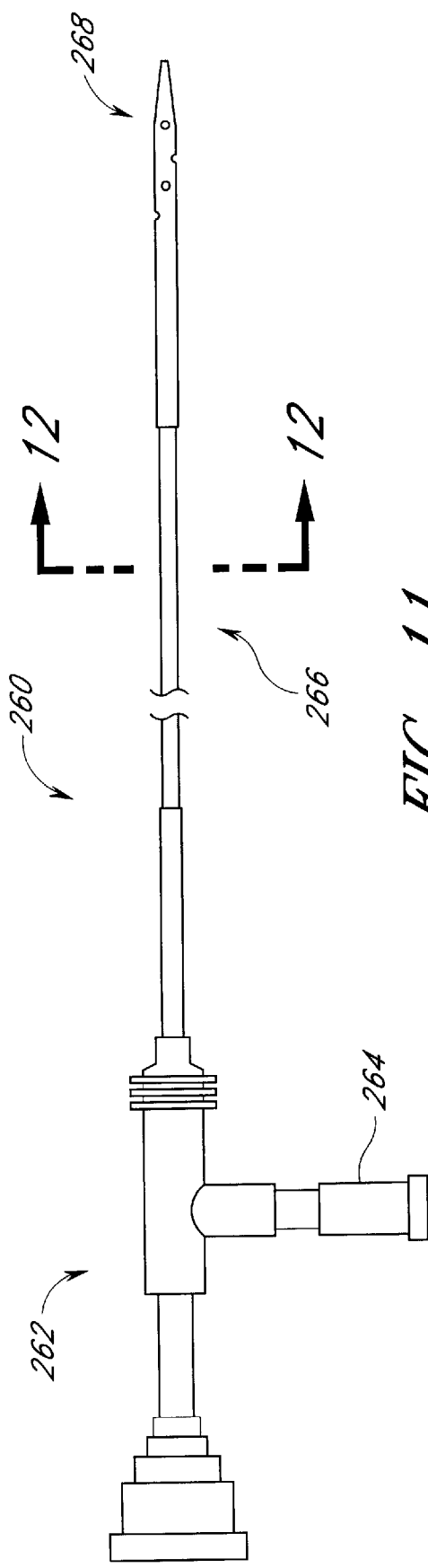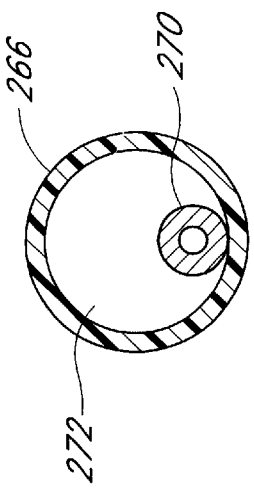
FIG. 11
FIG. 12
FIG. 13

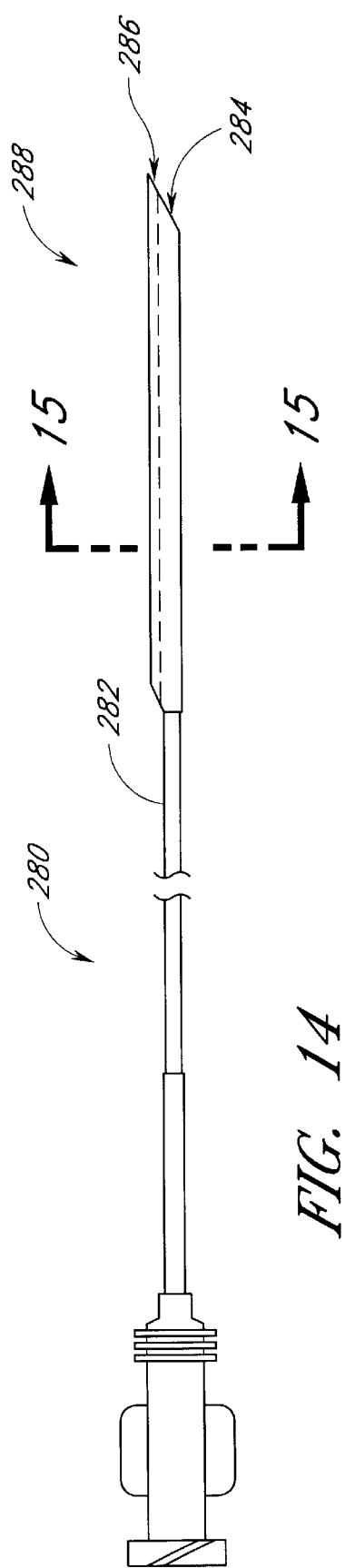
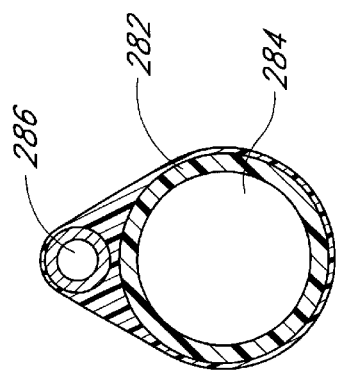
FIG. 14
FIG. 15

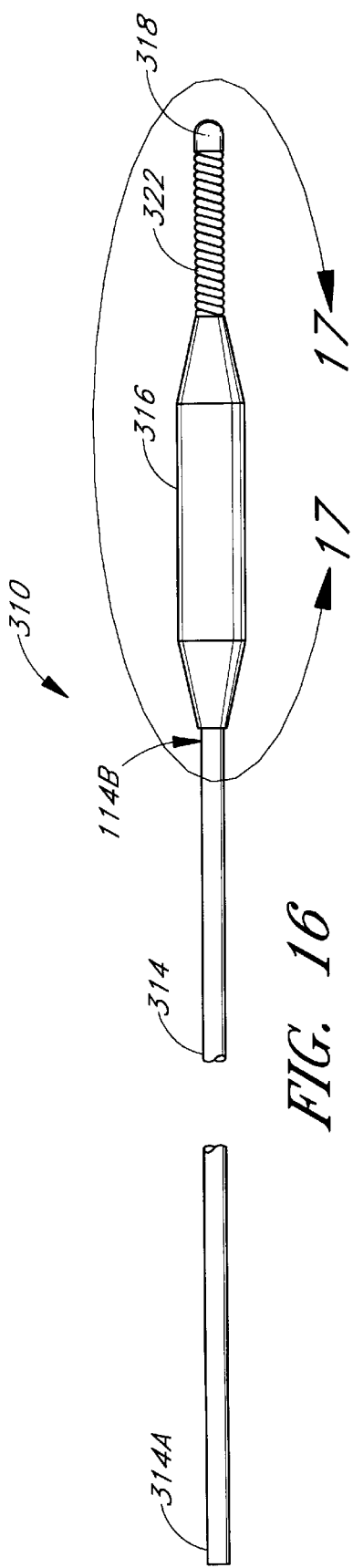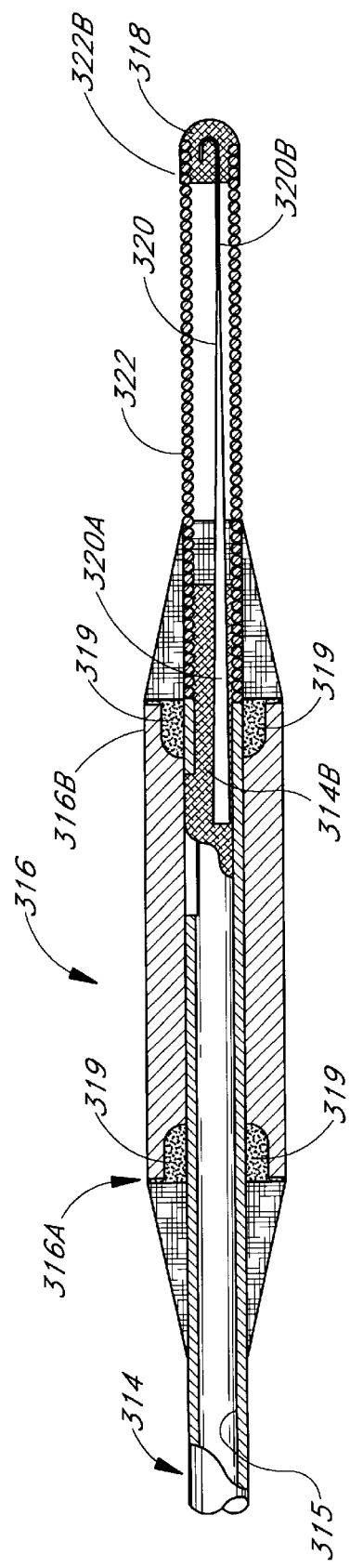

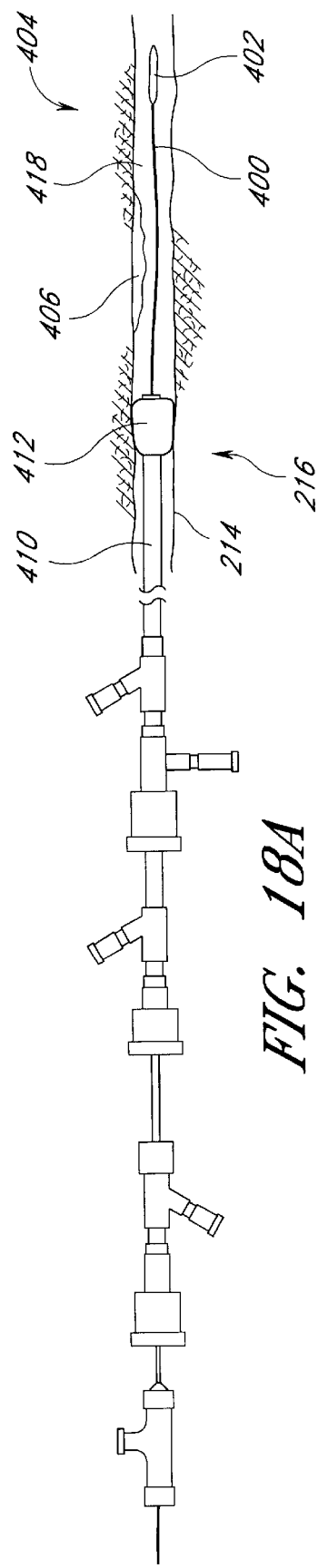
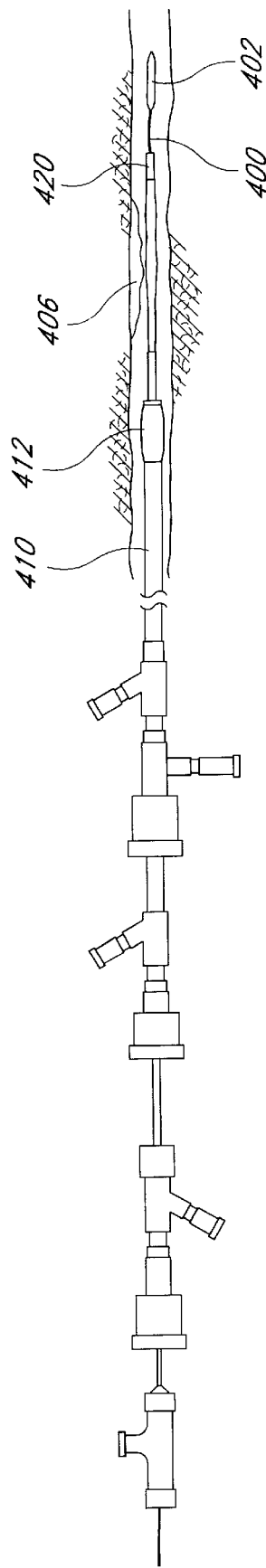
FIG. 18A
FIG. 18B

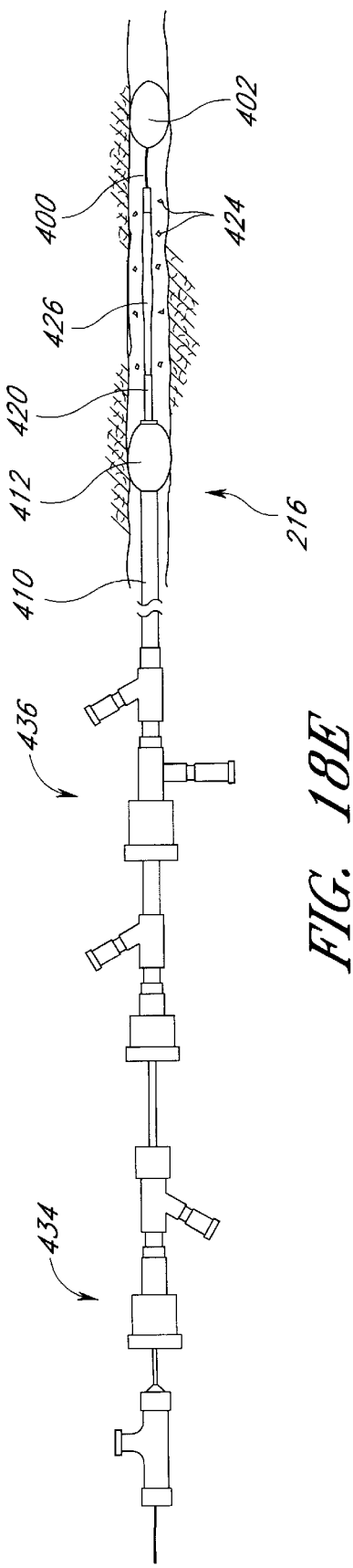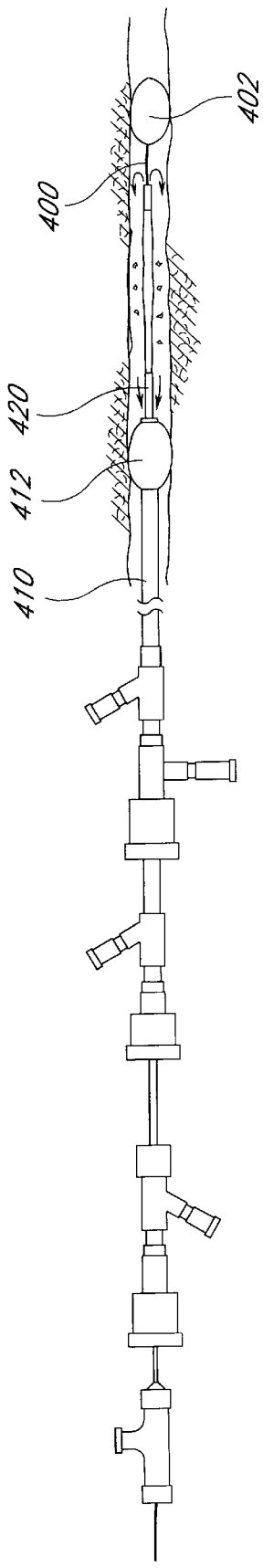

Flow Rate vs δp

Flow Rate Interaction Plot Between Irrigation and Aspiration Pressures

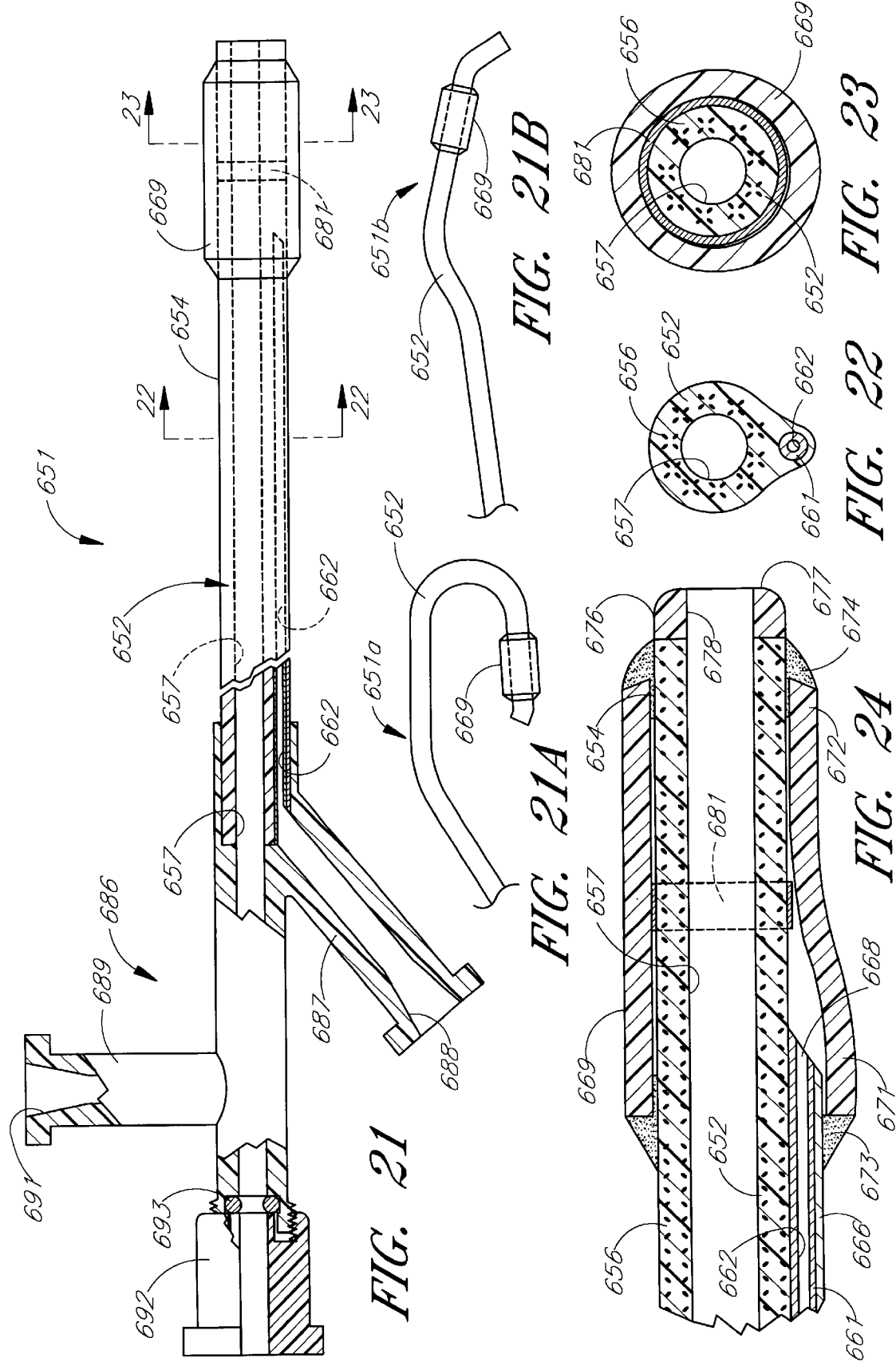

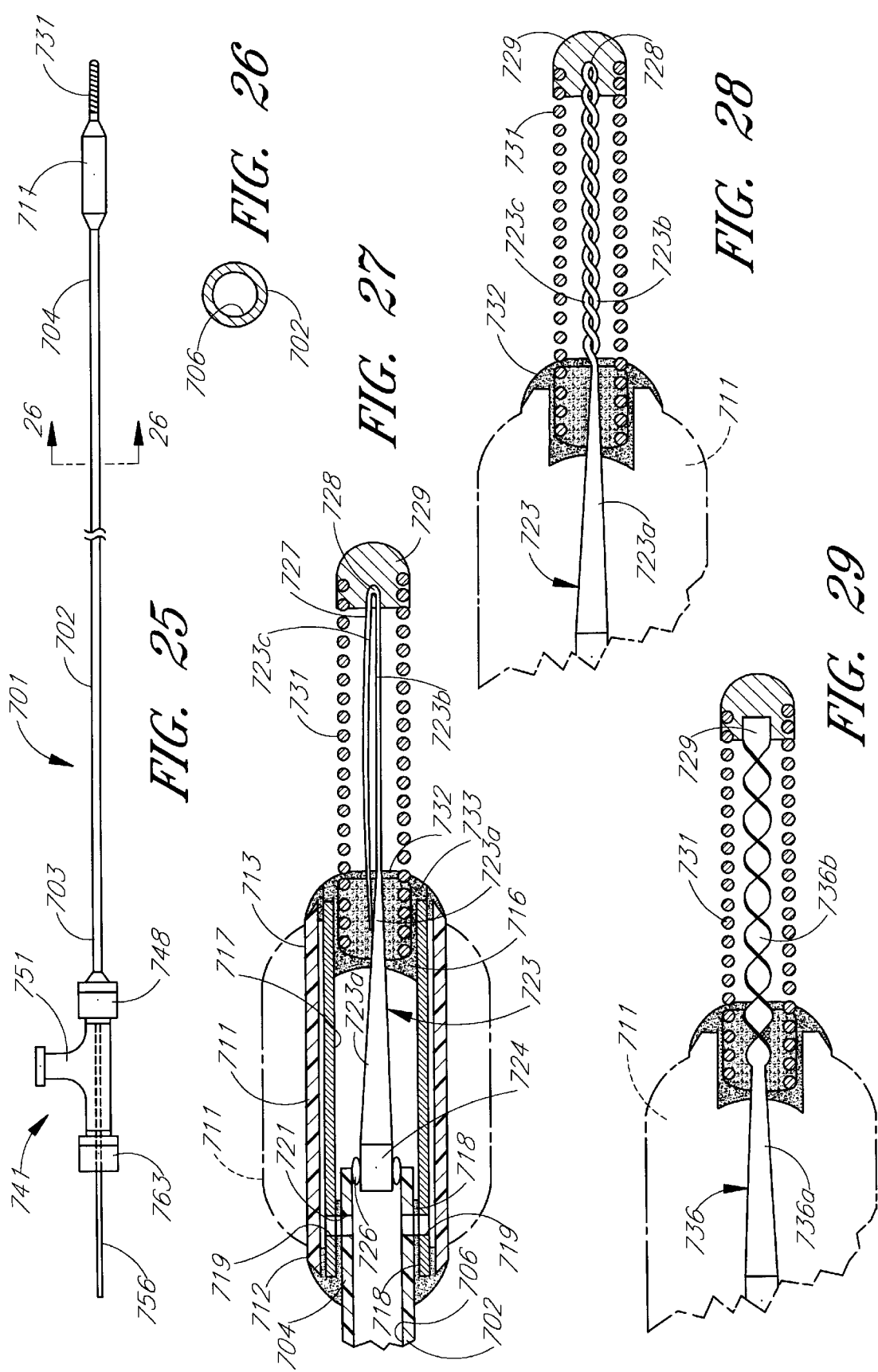

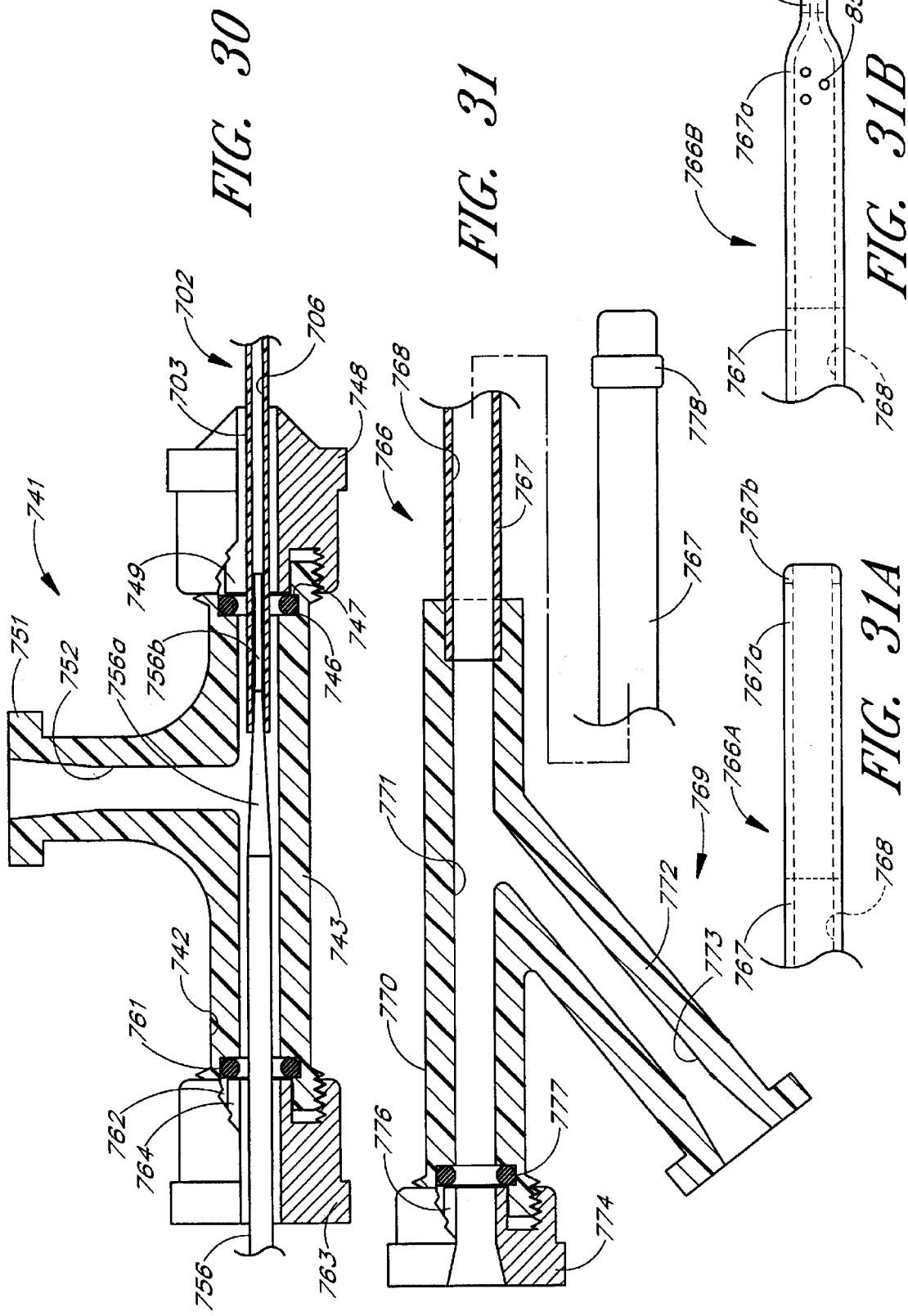

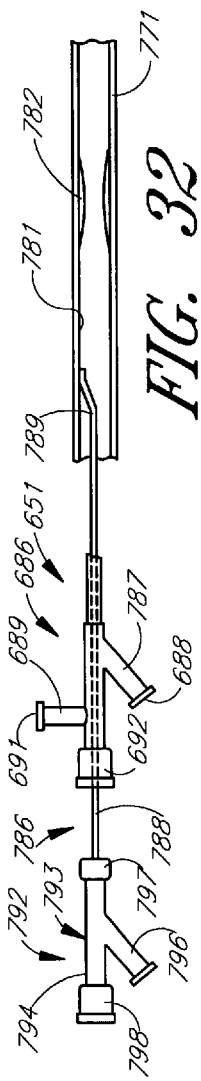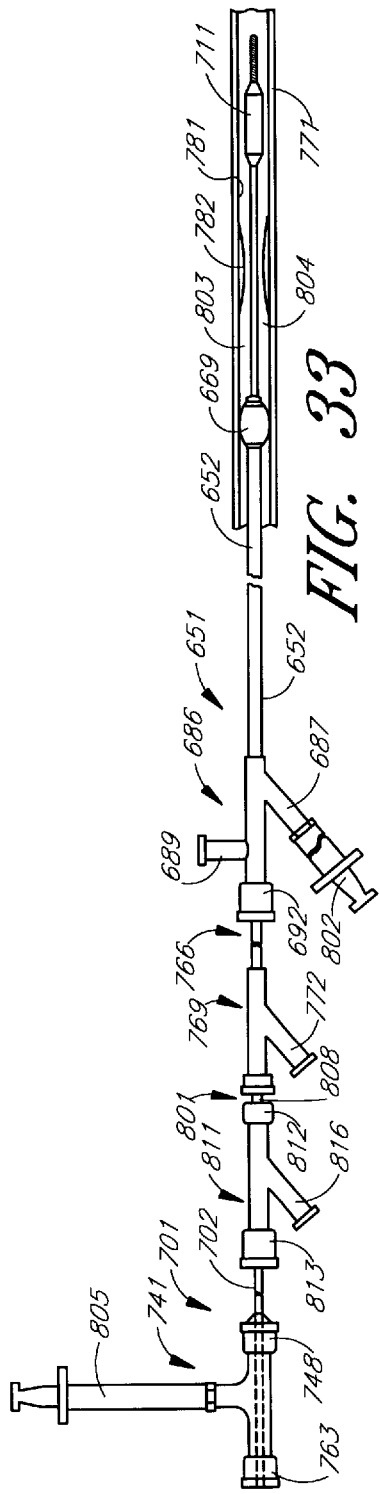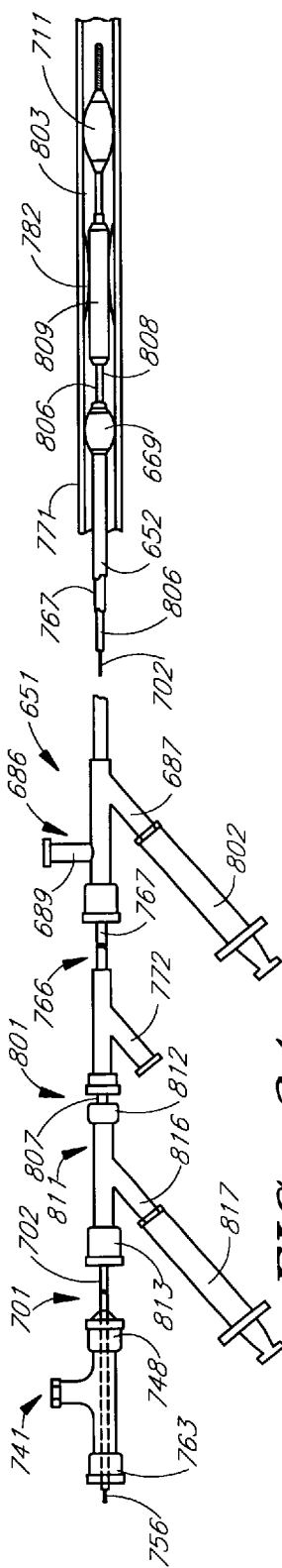

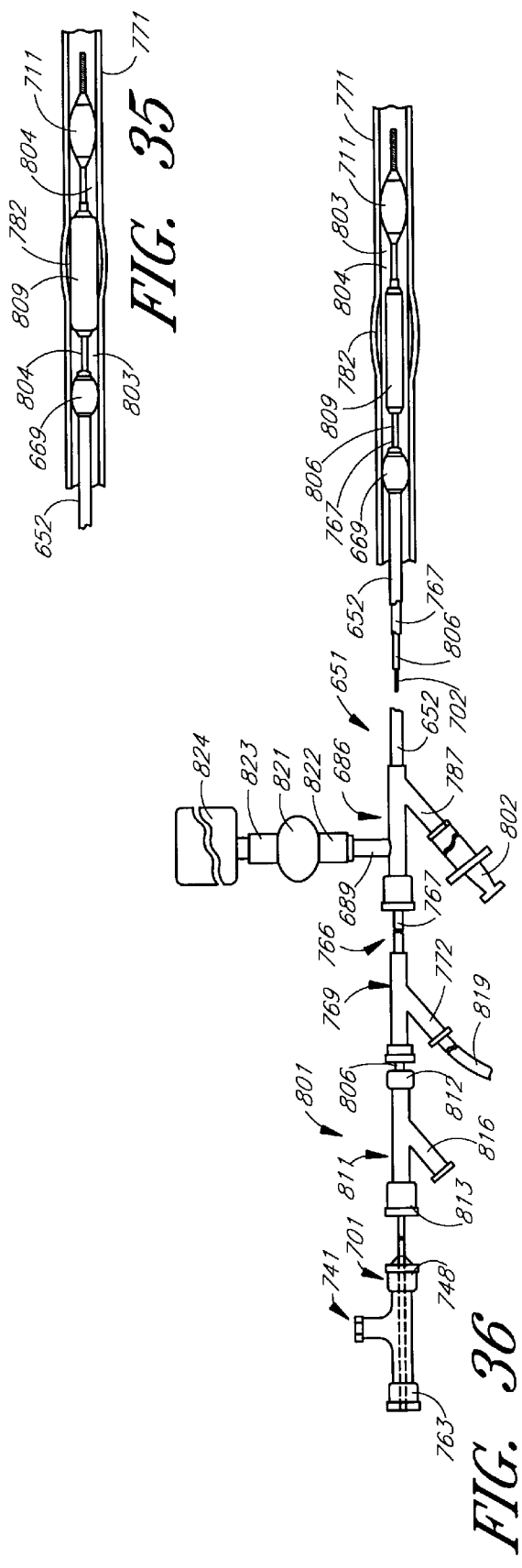
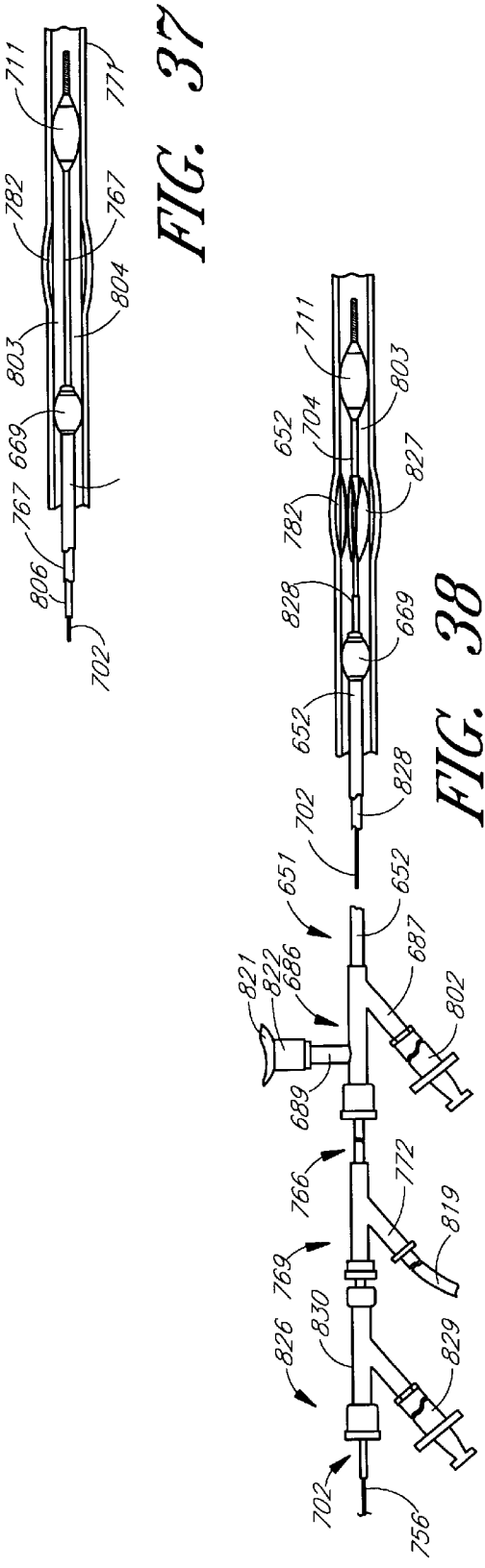
FIG. 35
FIG. 36
FIG. 37
FIG. 38

METHODS FOR EMBOLI CONTAINMENT

CROSS-REFERENCE TO RELATED APPLICATIONS

This application is a continuation of U.S. patent application Ser. No. 09/314,054, filed May 18, 1999, which is a continuation of U.S. patent application Ser. No. 08/812,570, filed Mar. 6, 1997, which issued as U.S. Pat. No. 6,022,336, which is a continuation-in-part of U.S. patent application Ser. No. 08/650,464, filed May 20, 1996, now abandoned, the entirety of which is incorporated by reference.

BACKGROUND OF THE INVENTION

1. Field of the Invention

The present invention relates generally to medical devices, and, in particular, to a system of improved irrigation and aspiration catheters used in the containment and removal of emboli resulting from therapeutic treatment of occlusions within blood vessels.

2. Description of Related Art

Human blood vessels often become occluded or blocked by plaque, thrombi, other deposits, or emboli which reduce the blood carrying capacity of the vessel. Should the blockage occur at a critical place in the circulatory system, serious and permanent injury, and even death, can occur. To prevent this, some form of medical intervention is usually performed when significant occlusion is detected.

Balloon angioplasty, and other transluminal medical treatments, are well-known, and have been proven efficacious in the treatment of stenotic lesions in blood vessels. The application of such medical procedure to certain blood vessels, however, has been limited, due to the risks associated with creation of emboli during the procedure. For example, angioplasty is not the currently preferred treatment for lesions in the carotid artery, because of the possibility of dislodging plaque from the lesion, which can enter the various arterial vessels of the brain and cause permanent brain damage. Instead, surgical procedures such as carotid endarterectomy are currently used, wherein the artery is split open and the blockage removed, but these procedures present substantial risks.

Other types of intervention for blocked vessels include atherectomy, deployment of stents, introduction of specific medication by infusion, and bypass surgery. Each of these methods are not without the risk of embolism caused by the dislodgement of the blocking material which then moves downstream. In addition, the size of the vessel may limit access to the vessel.

Thus, there is a need for a system to contain and remove such emboli. Various devices and methods have been proposed, but none have been especially commercially successful. Perhaps this is because a number of significant problems are faced in designing a system which will quickly and easily, yet effectively, evacuate emboli from a treatment location within a blood vessel. First, the small size of certain vessels in which such therapy occurs is a limiting factor in the design of emboli containment and removal systems. Vessels as small as 3 mm in diameter are quite commonly found in the coronary arteries, and even certain saphenous vein graph bypass vessels can also be as small as 3 mm or 4 mm; although some can range as high as 7 mm. Certain of the carotid arteries also can be as small as 4 mm in diameter; although, again, others are larger. Nevertheless, a successful emboli removal system must be effective within extremely small working areas. The system is equally effective in larger vessels, those of 5 mm or more in diameter.

Another obstacle is the wide variety in emboli dimensions. Although definitive studies are not available, it is believed that emboli may have approximate diameters ranging anywhere from tens of micrometers to a few hundred micrometers. More specifically, emboli which are considered dangerous to the patient may have diameters as large as 200 to 300 micrometers or even larger. Thus, an effective emboli removal system must be able to accommodate relatively large embolic particles and, at the same time, fit within relatively small vessels.

Another difficulty that must be overcome is the limited amount of time available to perform the emboli removal procedure. That is, it will be understood that in order to contain the emboli produced as a result of intravascular therapy, the vessel must be occluded, meaning that no blood perfuses through the vessel to the end organs. Although certain perfusion systems may exist or may be developed which would provide occlusion to emboli while permitting the substantial flow of blood, at present, the emboli may be contained only with a complete occlusion as to both blood flow and emboli escapement. Thus, again depending upon the end organ, the complete procedure, including time for the therapeutic treatment as well as exchanges of angioplastic balloons, stents, and the like, must be completed within just a few minutes. Thus, it would be difficult to include time for emboli removal as well. This is particularly true in the larger size vessels discussed above wherein a larger volume results in additional time required for emboli evacuation.

Moreover, it is important that an emboli containment and removal system be easy to use by physicians, and compatible with present therapeutic devices and methods. In addition, there are other difficulties which have made the successful commercialization of emboli containment and removal systems thus far virtually unobtainable.

SUMMARY OF THE INVENTION

The present invention advantageously satisfies the need in the prior art by providing a catheter system adapted to provide at least one pair of optimized paths for irrigation and aspiration fluid flow. Through careful design of the cross-sectional area of these paths, the present system is able to be compactly utilized in even the smaller size blood vessels. It can also be easily adapted to provide efficient and speedy emboli containment and evacuation in larger size vessels. This system is compatible with more common therapy devices in widespread use today, and is designed for rapid evacuation and ease of use.

It will be appreciated that, as used herein, the term "catheter" is broadly used to refer to a number of medical instruments, including without limitation, guidewires, therapy catheters, and the like. Thus, it is important in the present invention that the medical instruments used therein cooperate together to define optimized paths for irrigation and aspiration, as set forth herein in more detail.

Thus, in one embodiment of the present system, at least two catheters are utilized to form and evacuate a treatment chamber. Again, however, it will be appreciated that the term "chamber" refers broadly to a treatment location or site where therapy is performed and emboli possibly produced. The catheters of the present invention telescope one in another in order to form a pair of irrigation and aspiration paths. An outer, larger diameter catheter forms the main body or housing for the system. An inner, smaller diameter catheter is positioned within the lumen of the outer or main catheter. An optional intermediate, or middle catheter is positioned over the inner catheter so as to be within the space formed between the inner and outer catheters. Thus, in this embodiment, the catheters cooperate to form two irrigation/aspiration paths: one between the outer catheter and intermediate catheter, and one between the intermediate catheter and inner catheter. In another embodiment, these paths are formed by the annulus between each pair of respective catheters of the present system; although it will be understood that, in use, the catheters may not necessarily be positioned concentric one with another. Therefore, the term "annulus" is used in a broader sense to refer to the path or space between any two catheters.

In addition, rather than being telescoped, the innermost two catheters may be placed side-by-side within the main catheter. In this embodiment, less frictional losses are experienced by the fluid as it flows in and out of the irrigation/aspiration paths. Moreover, the intermediate catheter may take the form of a dedicated irrigation catheter or, conversely, a dedicated aspiration catheter. Likewise, the intermediate catheter may comprise a therapy catheter which rides over the inner catheter (which itself may take the form as a typical guidewire) to the treatment site, or the therapy catheter can be built over an aspiration catheter to provide another embodiment of the intermediate catheter. Since irrigation or aspiration can take place in the path between the inner catheter and the therapy catheter, less time is incurred in the emboli removal process, since the therapy catheter need not be removed in exchange for other types of catheters.

Alternatively, the intermediate catheter can be a single main catheter configured to provide both irrigation and aspiration. This catheter has two lumens, one of which can extend past the distal end of the catheter. One lumen can be used to provide irrigation, while the other provides aspiration. This dual lumen catheter can be configured such that at least a portion of the catheter rides over the inner catheter. Alternatively, the catheter can comprise a rheolitic device, or any other device capable of both treating and aspirating the occlusion. This would eliminate the need for a separate aspiration catheter, thus simplifying the procedure.

In another embodiment, once therapy has been performed, the therapy catheter is removed, and the patient's own blood acts as irrigation fluid. This eliminates the need for a separate irrigation catheter and irrigation fluid. Aspiration can occur through an aspiration catheter, or through the outer catheter. This reduces the time necessary to complete the procedure and reduces the number of necessary catheters.

Another aspect of the present invention is that the catheter system itself is provided with occlusive devices to form an emboli containment chamber. It will be noted that at least two such occlusive devices are needed to form a chamber in a straight vessel, while multiple occlusive devices may be necessary to provide emboli containment in the case of a branching vessel. Again, in this context, the term "occlusive device" makes reference to the blocking or containment of emboli within the chamber, since perfusion systems which provide occlusion to the emboli are within the scope of the present invention. Thus, various types of occlusive devices such as filters or expandable braids that allow particles of less than 20 micrometers to pass through while preventing the passage of larger particles, and including inflatable or expendable balloons such as those which are employed by the present catheter system or otherwise, are within the scope of the present invention. In one preferred embodiment, the outer catheter comprises a main catheter having an occlusive balloon mounted on the outer diameter thereof. The occlusive balloon is inflated by means of an inflation lumen formed in a wall of the main catheter. The inner catheter comprises what may be referred to as a guidewire, but which is also hollow to provide an inflation lumen for a second occlusive balloon mounted at the distal section thereof. This occlusive balloon remains inflated until the guide catheter crosses the site of the lesion within the vessel. Thus, when inflated, these two occlusion balloons form an emboli containment chamber. The inner catheter provides a guidewire for those types of therapy devices which are in common use. One such catheter for a dedicated irrigation/aspiration catheter is positioned over the guidewire to form one of the irrigation/aspiration paths therewith.

Another advantage of the present invention is that the catheters are sized so as to optimize the cross-sectional area of the irrigation/aspiration paths. Thus, a larger range of emboli sizes are capable of being evacuated. Moreover, irrigation or aspiration is possible through either path, depending upon the desired conditions or particular procedure being performed. Thus, the versatility of the present system allows, in one embodiment, aspiration to be performed through the outer path and irrigation to be provided through the inner path, or vice versa. It will be noted for clarity that "outer path" refers to that formed between the outer catheter and the intermediate catheter, while "inner path" refers to that formed between the inner catheter and intermediate catheter.

In another embodiment, the respective irrigation/aspiration cross-sectional areas are designed to balance and optimize flow. This balancing of the path areas not only allows the reversal of irrigation or aspiration, as explained above, but also improves the fluid mechanics exhibited by the system. That is, the flow of irrigation fluid within the vessel can be analogized to fluid flow within a pipe, with the entrance of the pipe being the mouth of the irrigation catheter and the exit of the pipe being the mouth of the aspiration catheter; it is the flow into the chamber versus the flow out of the chamber that creates the pressure within the chamber. Thus, a differential in pressure at the mouths of the irrigation and aspiration catheters will generate a flow rate used to evacuate the containment chamber. However, since flow rate varies with the product of fluid velocity in the cross-sectional area, for steady flow rate, it would be observed that decreases in the cross-sectional area of one of the irrigation/aspiration paths will produce an increase in fluid velocity. Since local pressure varies with the square velocity, such a reduced path cross-sectional area could produce an excessive pressure which may damage the vessel. Thus, it is desirable that local pressures in the vessel not exceed about 1.5 atmospheres (e.g., less than about 50 psi). In addition to possible damage, excessive pressures may simply cause the vessel to expand without resulting in any advantageous increase in flow rate. Thus, by optimizing the respective areas of the irrigation/aspiration paths, these parameters can be maintained within tolerable limits.

Increases in internal or local pressures also require substantial increases in external pressures. That is, in order to maintain the desired flow rates necessary to quickly and efficiently evacuate the containment chamber, as the cross-sectional area of the irrigation/aspiration paths are reduced, a greater change in pressure ($\Delta p$) is required to generate sufficient fluid velocity. Taking into consideration the frictional losses in the system, extremely high $\Delta p$'s may be required. Thus, it is important to maintain a balanced system so that excessive internal pressures are not produced, which may damage the vessel. Such pressures may also have the effect of causing a leak in the chamber.

Thus, the present invention provides a catheter system, comprising a hollow inner catheter having an occlusion device mounted on the distal end. At least a portion of an intermediate catheter is positioned over the inner catheter to create an inner fluid pathway for irrigation or aspiration. The intermediate catheter is slidable to a location proximal to the occlusion device on the inner catheter. A main catheter sized to receive the intermediate catheter such that an outer fluid pathway is formed therebetween for irrigation or aspiration. The main catheter also has an occlusion device mounted on its distal end which cooperates with the occlusion device on the inner catheter to form a chamber therebetween. The main catheter has an irrigation/aspiration port to permit irrigation or aspiration through its lumen. In one preferred embodiment, irrigation fluid is provided through the inner pathway and aspiration pressure is provided through the outer pathway.

The inner catheter is preferably a guidewire. The intermediate catheter can be an irrigation catheter, an aspiration catheter, a combined irrigation/aspiration catheter, or a therapy catheter, such as a drug delivery catheter, a laser, an ultrasound device, a thrombectomy catheter, a rheolitic device, a stent-deploying catheter, or any of a number of devices. The therapy catheter can be, for example, a balloon angioplasty catheter. Inflatable balloons can also be used as the occlusion devices on the inner and main catheters. To inflate the balloon, the main catheter can further comprise an inflation lumen located in the wall of the catheter in fluid communication with the inflatable balloon. The intermediate catheter can have both a main lumen and a separate lumen adjacent the main lumen sized to received the inner catheter slidably therein. The separate lumen can have a slit in an outside wall for insertion and removal of the inner catheter therethrough.

To fit in small blood vessels, it is preferred that the main catheter has an outer diameter of less than 5 mm. To provide efficient clearance of the emboli containment chamber, the inner pathway and the outer pathway should have an opening at their distal ends which act to balance fluid flows. In preferred embodiments, the inner pathway and the outer pathway each have an opening allowing the passage of particles of about 20 micrometers, up to those at least about 500 micrometers in diameter.

The system can include at least one additional inner catheter having an occlusion device mounted on its distal end sized to fit slidably within the intermediate catheter. This system can be used within branching blood vessels where more than one branch must be occluded to create an isolated chamber.

Accordingly, the catheter system of the present invention provides an improved emboli containment and removal system which can be utilized in a wide range of vessel diameters, including extremely small ones. The system is easy to use and can quickly and efficiently evacuate the treatment chamber.

BRIEF DESCRIPTION OF THE DRAWINGS

FIG. 3 is a side view of the main catheter for use in the present invention.

FIG. 4 is a cross-sectional view of the main catheter taken along line 4—4 of FIG. 3.

FIG. 5 is a cross-sectional view of the main catheter taken along line 5—5 of FIG. 3.

FIG. 7 is a side view of a single operator irrigation catheter for use in the present invention.

FIGS. 8 through 10A are cross-sectional views of the single operator catheter taken along lines 8—8, 9—9 and 10A—10A of FIG. 7.

FIG. 10B is a cross-sectional view of the single operator catheter inserted within the main catheter, illustrating schematically the inner and outer paths which are formed by the catheter system of present invention.

FIG. 11 is a side view of an over-the-wire aspiration catheter for use in the present invention.

FIG. 12 is a cross-sectional view of the over-the-wire aspiration catheter taken along line 12—12 in FIG. 11.

FIG. 13 is a cross-sectional view of the over-the-wire aspiration catheter taken along line 12—12 in FIG. 11, showing a guidewire inserted therethrough.

FIG. 14 is aside view of a single operator aspiration catheter for use in the present invention.

FIG. 15 is a cross-sectional view of the single operator aspiration catheter taken along line 15—15 of FIG. 14.

FIG. 16 is a side view of an inner catheter for use in the present invention.

FIG. 17 is a is a partial cross-sectional view of the inner catheter taken along line 17—17 of FIG. 16.

FIGS. 18A–H illustrate the use of the catheters of the present invention in emboli containment treatment procedures.

FIG. 21 is a side-elevational view of a main catheter and

FIGS. 21A and 21B are partial side-elevational views of the distal extremities showing alternative embodiments of the main catheter incorporating, respectively, Judkins left shape and Judkins right shape in their distal extremities.

FIG. 22 is a cross-sectional view taken along the line 22—22 of FIG. 21.

FIG. 23 is a cross-sectional view taken along the line 23—23 of FIG. 21.

FIG. 24 is an enlarged partial cross-sectional view of the distal extremity of the catheter shown in FIG. 21.

FIG. 25 is a side-elevational view of the balloon-on-a-wire construction incorporating the present invention.

FIG. 26 is a cross-sectional view taken along the line 26—26 of FIG. 25.

FIG. 27 is an enlarged cross-sectional view of the distal extremity of the construction in FIG. 25.

FIG. 28 is a cross-sectional view similar to FIG. 27 but showing a different embodiment utilizing a twisted dual core.

FIG. 29 is a cross-sectional view similar to FIG. 27 but showing the use of a twisted core.

FIG. 30 is a cross-sectional view of the proximal removable fitting of the construction shown in FIG. 25.

FIG. 31 is a side-elevational view partially in cross section of an irrigation catheter incorporating the present invention.

FIGS. 31A and 31B are side-elevational views of the distal extremities of additional embodiments of irrigation catheters incorporating the present invention.

FIGS. 32–38 illustrate the manner in which the apparatus of the present invention shown in FIGS. 21–31 is used performing a therapeutic procedure in accordance with the present invention.

DETAILED DESCRIPTION OF THE PREFERRED EMBODIMENT

The present invention provides a system of improved irrigation and aspiration catheters used in the treatment of occlusions within blood vessels and emboli containment. The apparatus of the present invention are adapted for use in the treatment of an occlusion in a blood vessel in which the occlusion has a length and a width or thickness which at least partially occludes the vessel's lumen. It is to be understood that "occlusion" as used herein, includes both complete and partial occlusions, stenoses, emboli, thrombi, plaque, and any other substance which at least partially occludes the lumen of the blood vessel.

Emboli Containment and Removal

Figure 1:
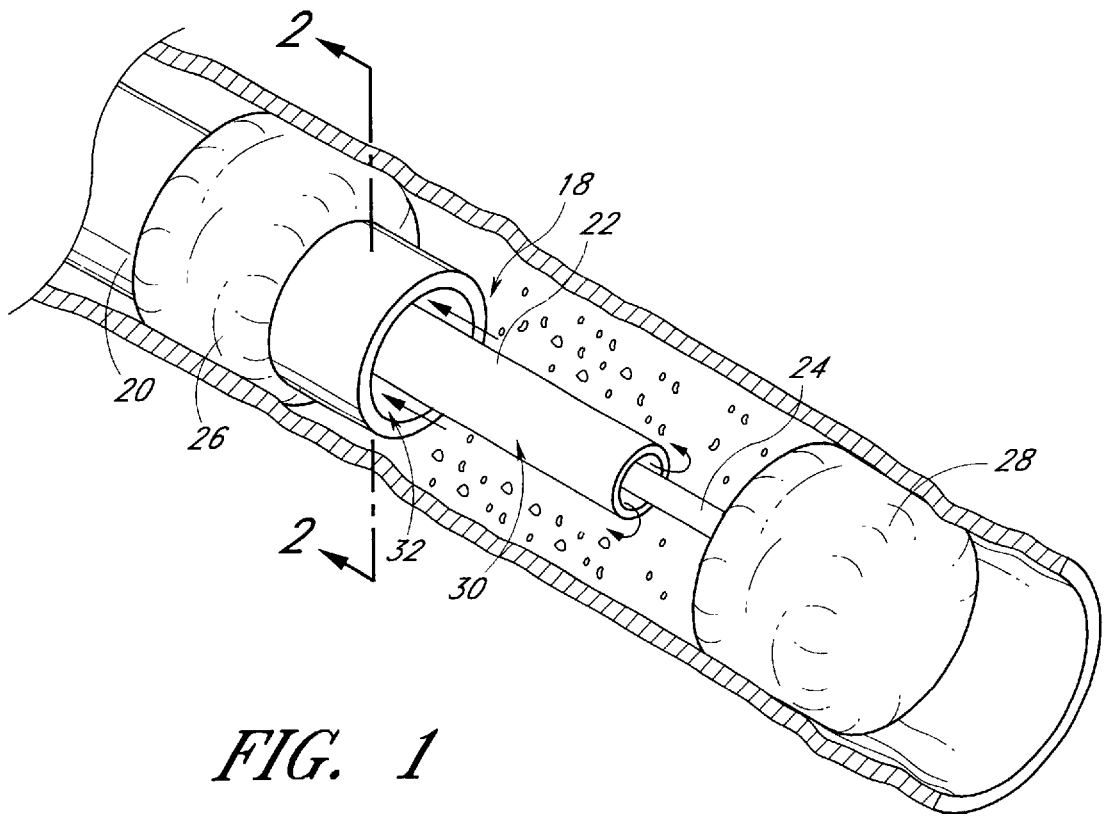
FIG. 1 is a schematic illustration of the catheter system of the present invention illustrating the manner in which an emboli containment chamber is formed.

Referring to FIG. 1, there is shown a schematic illustration of the catheter system of the present invention and the manner in which it forms an emboli containment chamber for efficient emboli removal. The catheter system, in this embodiment, comprises a three-catheter system, including an outer or main catheter 20, an intermediate catheter 22, and an inner or guidewire catheter 24. This catheter system is shown schematically inserted within a relatively small vessel having a diameter d. As set forth above, the diameter d of the vessel may be as small 3 mm to 4 mm; although the present, system can be efficiently utilized within vessels of larger diameter. An emboli containment chamber is formed between the outer 20 and inner 24 catheters, each of which in the preferred embodiment are provided with inflatable occlusion balloons 26 and 28. As noted above, the present invention is compatible with other types of occlusive devices, including those which permit perfusion and those which have other deployment mechanisms, such as filters, braids and the like. The present system is also compatible with containment chambers of variable length. Chambers of longer lengths contain a large volume of fluid and, thus, increase the time for emboli evacuation and/or increase the pressure differential (Δp) required to achieve desirable evacuation flow rates. Thus, containment chambers in the range of about 0.3 cc to 30 cc are preferable.

Although FIG. 1 illustrates the present catheter system deployed within a straight vessel, it will be understood that the principles of the present invention also include other vessel configurations, including branches vessels. In such cases, a third or even additional occlusive devices may be used in order to contain the emboli and form a working chamber. Such occlusive devices could be mounted on additional inner catheters similar to the one illustrated in FIG. 1, or on a single inner catheter having itself two branches, or otherwise. FIG. 1 illustrates an important feature of the present invention in which the catheters 20, 22, 24 are telescoped within one another. Thus, the inner catheter 24 is relatively small in outer diameter and fits within the inner diameter of the intermediate catheter 22 and can, in some applications, serve as a guidewire therefor. Likewise, the outer diameter of the intermediate catheter 22 fits within the inner diameter of the outer or main catheter 20. The catheters 20, 22, and 24 thus form inner and outer pathways, 30 and 32 between the inner 24 and intermediate 22 catheters and the intermediate 22 and outer 24 catheters, respectively. It is through these pathways 30, 32 that irrigation or aspiration may be performed. Advantageously, in the present system, irrigation can be performed through the inner pathway 30 and aspiration through the outer pathway 32, or vice versa. As explained below in more detail, irrigation refers to the injection of fluid through one of the pathways into the containment chamber in order to generate an evacuation flow rate. Fluid, together with emboli, are evacuated through the other pathway, being assisted by the aspiration pressure which is in reality a suction or negative pressure. It is this pressure differential over some length within the chamber which generates the evacuation fluid flow.

Figure 2:
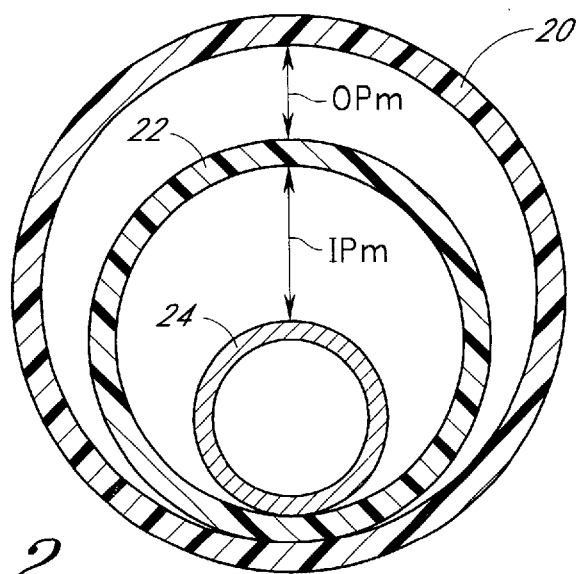
FIG. 2 is a cross-sectional view taken along line 2—2 of FIG. 1 illustrating schematically one embodiment of the irrigation and aspiration paths which are formed by the catheter system of present invention.

As merely one example, irrigation fluid could be supplied at one pressure through the irrigation pathway as indicated by the small arrows in FIG. 1. Due to the pressure differential in the chamber, fluid begins to flow toward the outer pathway, being assisted by the negative aspiration pressure. Thus, emboli in the chamber are swept through the outer pathway indicated by the arrows. Accordingly, FIG. 1 illustrates one catheter arrangement of the present invention in which the catheters 20, 22, 24 are telescoped one inside the other; although the principles of the present invention apply equally well to other nontelescoped catheter configurations. Also, as noted above, other types of catheters may be used in connection with the present system. FIG. 2 illustrates a cross-sectional view of the present catheter system taken along lines 2—2 of FIG. 1, and illustrates in further detail relative cross-sectional dimensions of the inner and outer pathways. However, it will be noted that FIG. 2 is schematic in the sense that it illustrates the inner 24 and intermediate 22 catheters positioned at the bottom of the lumen of the outer catheter 20. This is for ease of illustration only, as it will be understood that in actual practice the positions of the various catheters 20, 22, 24, relative one to another may vary due to pressures, flow rates, etc. The catheters 20, 22, 24 of the present system are designed so as to compactly fit within even small diameter vessels and at the same time optimize the cross-sectional areas of the inner and outer pathways. This design criteria, for a given flow rate, can be expressed as follows:

$$Q = \frac{Dp\pi d^4}{128L\mu}$$

where:

Q=flow rate

Dp=pressure differential between the proximal and distal ends of the catheter

D=net diameter of the catheter

L=the overall length of the catheter $\mu$=the viscosity of the fluid

128=constant factor

Thus, when a particular desired flow rate is known, the foregoing equation can be solved for D to give an optimized inner diameter of the intermediate catheter 22 when empty, or an equivalent diameter when the inner diameter is partially occluded by, for example, the inner catheter. It will be noted that the diameter of the intermediate catheter 22 is perhaps the more sensitive design parameter since, as it increases or decreases the cross-sectional areas of the inner and outer pathways increases and decrease, respectively. Furthermore, the other parameters in the equation are often given, including the external pressure differential, the length of the intermediate catheter 22 (which is typically about 100–120 cm) and the viscosity of the fluid. As for the desired flow rate, it will be understood that merely one flushing of the containment chamber may not be sufficient to remove all emboli. This is because of the relatively high viscosity of the patient's blood in the chamber and the inertia of the emboli which must be overcome. Also, as set forth above, some emboli are relatively large in diameter requiring several flushes. Thus, preferably, the flow rate will be such that the fluid in the containment chamber is changed at least about twice within a two- or three-minute period, while maintaining the local pressure in the chamber within a safe range (less than about 50 psi). Preferably, the fluid will be changed as many as five times or more within a minute in order to reduce the overall treatment time in connection with these procedures.

It will be understood that FIG. 2 illustrates an ideal condition in which size of the openings of the inner and outer pathways are maximized. As this illustration does not always represent actual conditions, emboli size must be taken into consideration. Thus, the maximized opening for the inner and outer pathways ($ip_m$ and $op_m$) should be at least about 150 micrometers and more preferably about 1000 micrometers. Thus, in the minimum state, where all of the catheters 20, 22, 24 are approximately concentric with one another, $ip_m$ and $op_m$ will range between about 250 and 500 micrometers. Thus, good evacuation performance should still be attainable.

In one embodiment of the present system, described below in more detail in connection with an irrigation and aspiration study, a catheter system found to be suitable comprised an outer catheter 20 with an inner diameter of 0.086" and an intermediate catheter 22 with inner and outer diameters of 0.048" and 0.054", respectively. The inner catheter 24 comprises a guidewire of typical outer diameter of about 0.014" but can be as large as 0.038". Converting these dimensions to micrometers yields a total inner diameter of the outer catheter 20 of about 2200 micrometers, an outer diameter of the inner catheter 24 of about 355 micrometers, and a wall thickness of the intermediate catheter 22 of about 150 micrometers. This leaves a maximum inner pathway opening ($ip_m$) of about 770 micrometers and the maximum outer pathway opening ($op_m$) of about 800 micrometers. This will be sufficient to remove even larger sized emboli. This example also illustrates a catheter system configuration in which the respective cross-sectional areas of the inner and outer pathways are similar, thus yielding a balanced pressure differential condition in the containment chamber. By eliminating the use of the intermediate catheter, as explained below, the opening of the outer pathway can be increased even more.

Catheter Construction

Outer Catheter

FIG. 3 illustrates a side view of a catheter which can be used as the outer catheter of the present system. Catheter 110 generally comprises an elongate flexible tubular body 116 extending between a proximal control end 112 and a distal functional end 114. The tubular body 116 has a main lumen 130 which extends between the ends 112 and 114. The main lumen 130 terminates in a proximal opening 123 and a distal opening 127. A smaller inflation lumen 132, configured in a side-by-side relationship with the main lumen 130, extends along the length of the tubular body 116, and terminates within an occlusion balloon 126 mounted on the distal end 114 of the catheter 110, as described below. The inflation lumen 132 is in fluid communication with the occlusion balloon 126, such that fluid passing through the inflation lumen 132 may be used to inflate or deflate the balloon 126. The inflation lumen can terminate at its proximal end at one of the ports 122, 124 on the catheter 110.

The tubular body 116 must have sufficient structural integrity, or "stiffness," to permit catheter 110 to be advanced through vasculature to distal arterial locations without buckling or undesirable bending of tubular body 116. However, it is also desirable for tubular body 116 to be fairly flexible near its distal end 114, so that the tubular body 116 may be navigated through tortuous blood vessel networks. Thus, in one preferred embodiment, the body 116 is made to have variable stiffness along its length, with the proximal portion of the body 116 being less flexible than the distal portion of the body 116. Advantageously, a tubular body 116 of this construction enables a clinician to more easily insert the catheter into blood vessel networks difficult to reach by catheters having uniform stiffness. This is because the stiffer proximal portion provides the requisite structural integrity needed to advance the tubular body 116 without buckling, while the more flexible distal region is more easily advanced into and through tortuous blood vessel passageways.

In one preferred embodiment, variable stiffness along the length of the tubular body 116 is achieved by forming a polymeric tubular body 116 which incorporates a reinforcement along its length. Such reinforcement can be a braid or coil formed of various metals or polymers. The body 116 may be provided with a reinforcement incorporated into its wall structure. To achieve variable stiffness, the proximal region of the catheter 110 can be provided with greater reinforcement than the distal region.

The precise density of the braiding or pitch of the coil provided to the proximal and distal regions can be varied considerably at the point of manufacture, such that catheters having a variety of different flexibility profiles may be created. Moreover, the braid density or coil pitch may be varied within the various catheter regions, by providing a reinforcement that has a density or pitch gradient along its length.

A variety of different materials, known to be ductile and shapeable into fine wires, may be used to form the reinforcement, such as various polymers, stainless steel, gold or silver plated stainless steel, ELGILOY, platinum or nitinol. The reinforcement may be introduced into the structure of the catheter body 116 through conventional catheter forming techniques. Moreover, any of a variety of different polymeric materials known by those of skill in the art to be suitable for catheter body manufacture may be used to form the tubular body 116. Different materials might also be combined to select for desirable flexibility properties.

Also, although the tubular body 116 has been described in the context of having two regions of differing flexibility, it will be readily appreciated by those of skill in the art that three or more regions of differing flexibility may easily be provided, by adapting the teachings contained herein.

A control manifold 119 is provided at the proximal end 112 of the catheter 110. The control manifold 119 is generally provided with a number of ports to provide access to the catheter lumen 130. For example, for the embodiment depicted in FIG. 3, the control manifold 119 is provided with a catheter end-access port 122 and a catheter side-access port 124, to provide an introduction point for the insertion of other catheters into the lumen 130. Ports 122 and 124 are preferably provided with standard Touhy Borst connectors, although other types of connectors may be used. An inflation port 118, in fluid communication with the small inflation lumen 132, is further provided on the manifold 119 for attachment of devices to inflate or deflate the balloon 126. The manifold 119 is also provided with an irrigation/aspiration port 120 which is in fluid communication with the lumen 130, for attachment of devices to provide irrigation fluid or aspiration pressure. Other embodiments of the main catheter 110 may feature more or less ports, depending upon the number of lumen in the catheter and the desired functionalities of the catheter.

The manifold 119 is preferably formed out of hard polymers or metals, which possess the requisite structural integrity to provide a functional access port to the catheter lumen, such as for balloon inflation or delivery of irrigation fluid and/or aspiration pressure. In one preferred embodiment, the manifold 119 is integrally formed out of polycarbonate. Of course, any suitable material may be used to form the manifold 119.

The manifold 119 is attached to the tubular body 116 so that the various ports are placed in communication with the appropriate lumen, as described above in connection with FIG. 3. Preferably, a strain relieving connector 111 is used to join the manifold 119 to the tubular body 116. For the embodiment depicted in FIG. 3, the strain relieving connector 111 consists of a length of flexible polymeric tubing, such as polyethylene terephthalate (PET). The tubular body 116 is inserted in one end of the strain relieving connector 111, and the other end of the strain relieving connector 111 is inserted into the manifold 119. A suitable adhesive, such as a cyanoacrylate, may be used to bond the manifold 119 to the strain relieving connector 111. Adhesives may also be used to bond the strain relieving connector 111 to the tubular body 116, or alternately, conventional heat bonding, as known to those of skill in the art, may be used to attach the tubular body 116 to the strain relieving connector 111.

Although not required, the interior surface of the lumen 130 may be provided with a liner 135 formed of a lubricous material, to reduce the frictional forces between the lumen surface and the catheters which are inserted into the lumen 130. In one preferred embodiment, the liner 135 is formed out of polytetrafluoroethylene (PTFE). Materials other than PTFE, which are biocompatible, fairly flexible, and easily mounted to other polymeric materials of the type used to form catheter tubular bodies, may also be used to form the liner 135.

To minimize the outer diameter of the tubular body 116, it is preferable that the inflation lumen 132 be as small as possible in accordance with its function. That is, the inflation lumen 132 is preferably no larger than required to provide sufficient fluid to the occlusion balloon 126 for rapid inflation, or so that fluid may be quickly withdrawn from the balloon 126 during deflation. For compliant expansion balloons of the type described below, inflation lumen diameters of from about 0.006 inches to about 0.020 inches are satisfactory, with a diameter of about 0.010 inches being optimal.

Furthermore, in one embodiment, as illustrated in FIGS. 3–5, the outer diameter of the tubular body 116 just proximal to the balloon 126 is minimized by providing an inflation lumen 132a with an oval cross-sectional configuration, as illustrated in FIG. 5. Preferably, this inflation lumen 132a has an oval cross-sectional configuration which extends proximally from the proximal end of the balloon 126 by a distance of at least 0.1 cm, more preferably 1 cm, and optimally by a distance equal to the length of the tubular body. For ease of manufacturing, the cross-sectional configuration of the lumen 132 at points further proximal to the balloon 126 may be generally circular, as illustrated in FIG. 4. Where the lumen configuration differs from proximal to distal end, as illustrated in FIGS. 4 and 5, a region of transition 133 is provided wherein the lumen configuration changes from circular to oval.

As illustrated in FIG. 3, an inflatable balloon 126 is mounted on the distal end 114 of the catheter 110. In most applications where the catheter 110 is to be used in an emboli containment treatment procedure, the inflatable balloon 126 will function as an occlusion balloon, to prevent blood from passing through the blood vessel distal of the balloon 126. Thus, the inflatable balloon 126 is preferably able to expand to fit a variety of different blood vessel diameters. Accordingly, it is preferred that the inflatable balloon 126 have a compliant expansion profile, tending to increase in radial diameter with increasing inflation pressure. To achieve this, the balloon 126 may be made out of materials which impart such expansion characteristics, including elastomeric materials such as latex or irradiated polyethylene. In one preferred embodiment, the inflatable balloon 126 is formed out of a material comprising a block copolymer of styrene-ethylene-butylene-styrene, sold under the trade name C-FLEX. Further details as to balloons of this type are disclosed in U.S. Pat. No. 5,868,705, the entirety of which is incorporated by reference.

The inflatable balloon 126 can be placed in fluid communication with the lumen 132a via a fill hole (not shown) extending through the tubular body 116 within the balloon 126, such that fluid may be introduced into the lumen 132 through an inflation port 118 to inflate the balloon 126. Alternately, the lumen 132a may terminate within the balloon 126, to provide the requisite fluid communication. The balloon 126 may be attached to the tubular body 116 by any suitable manner known to those of skill in the art, such as adhesives or heat bonding.

Intermediate Catheter

Figure 6:
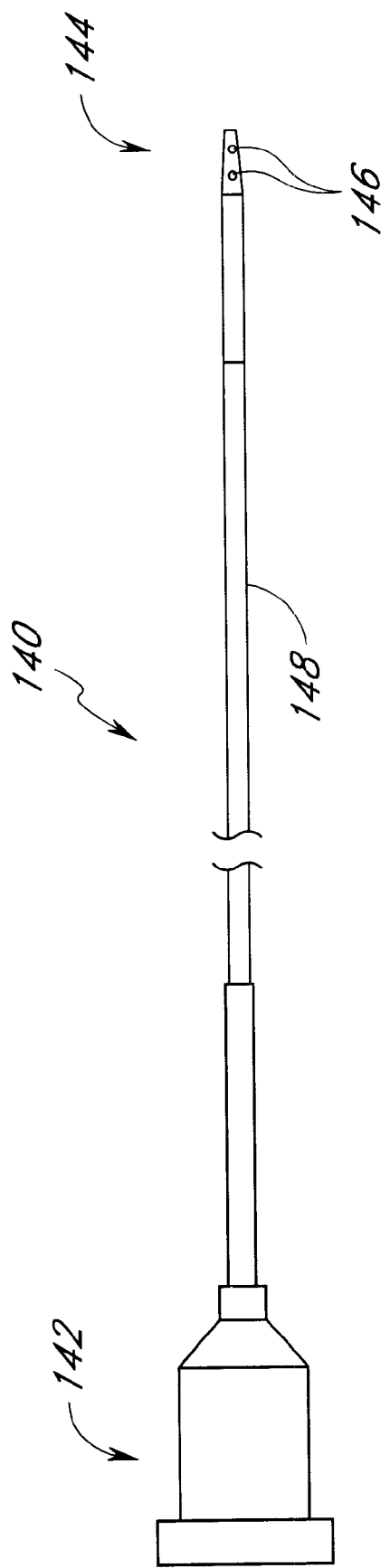
FIG. 6 is a side view of an over-the-wire irrigation or aspiration catheter for use in the present invention.

FIG. 6 is a side view of an irrigation or aspiration catheter 140 which may be utilized as the intermediate catheter. It should be understood that when an irrigation catheter is used for the intermediate catheter, aspiration occurs through the outer pathway between the intermediate and main catheters, while irrigation occurs through the inner pathway. When an aspiration catheter is used as the intermediate catheter, aspiration occurs through the inner pathway between the inner and intermediate catheters, while irrigation occurs through the outer pathway. Irrigation fluid under pressure is supplied at the proximal end of the catheter 142 and delivered into the containment chamber through the side holes 146 and through the distal end of the chamber 144. Alternatively, aspiration or negative pressure can be provided at the proximal end of the catheter 142 and fluid and debris aspirated through the side holes 146 and the distal end of the catheter 144. The catheter 140 may be about 125 cm in length and constructed from a plastic material such as HYTREL tubing, high density polyethylene (HDPE) or PEBAX (Atochem, France). In order to achieve a softer distal section, the durometer of the tube 148 material is reduced in that area to about 55 whereas that of the proximal section 142 is higher, such as about 80. The distal opening is preferably about 0.040", and the outer diameter is preferably about 0.065". Proximal valves and fittings which are well known in the art can be mounted on the irrigation catheter 140 of FIG. 6. This catheter can be of either over-the-wire (as shown) or single operator design, as explained in more detail below.

FIGS. 7–10A illustrate another type of irrigation or aspiration catheter 230 which can be used as the intermediate catheter of the present system. In the case of the irrigation catheter, irrigation is through the inner pathway and aspiration is through the outer pathway. If the catheter is used for aspiration, aspiration is through the inner pathway and irrigation is through the outer pathway. As shown in FIGS.

7–10A, the catheter 230 has an adaptor 232 on its proximal end. This single operator catheter 230 further comprises a long tubular body 236 having a distal end 238. The distal tip 238 can include a radiopaque marker to aid in locating the tip 238 during insertion into the patient, and is preferably soft to prevent damage to the patient's vasculature. At the distal end of the shaft 238, an inner catheter lumen 240 is attached. This lumen 240 provides a separate lumen, apart from the main lumen 242 of the catheter 230, for the insertion of the inner catheter. The inner diameter of the inner catheter lumen ranges from about 0.016" to about 0.020" for use with a 0.014" inner catheter system. In a preferred embodiment, the inner diameter of the lumen is about 0.019 in. This inner catheter or guidewire lumen can be as short as 5 cm, but can extend 30 cm or longer in a proximal direction. During delivery of the catheter 230, the proximal end of the inner catheter is inserted into the distal end of the inner catheter lumen 240, and the lumen 240 is slidably advanced over the inner catheter. Only a short segment of the single operator catheter 230 rides over the inner catheter, and the inner catheter remains in the lumen 240 and does not enter the main lumen 242 of the catheter 230.

Although the inner catheter lumen 240 is shown in FIG. 7 as being located only on the distal end 238 of the shaft of the catheter 236, the lumen 240 can also be made to extend the entire length of the shaft 236 if desired. In both embodiments, the main lumen 242 is advantageously left completely unobstructed to provide more efficient irrigation or aspiration. The inner catheter lumen 240 can also include a slit 241 or weakened area in the outside wall of the lumen 240 along the entire length of the lumen 240 to facilitate faster and easier insertion and removal of the inner catheter through the side wall of the lumen 240. By inserting and removing the inner catheter through the side wall of the lumen 240 on the catheter 236, the need to remove adapters and attachments from the proximal end prior to slidably advancing or removing the catheter 236 over the inner catheter is eliminated. It should be understood that this slit 241 or weakened area through which the inner catheter can be inserted and removed can exist on the intermediate catheter regardless of whether the catheter is used for irrigation, aspiration, therapy or some other purpose.

FIG. 10B is a cross-sectional view of a single operator intermediate catheter 252 positioned within the main catheter 250. The separate lumen 254 adapted to receive the inner catheter is positioned adjacent the lumen of the intermediate catheter 252. It should be understood that this positioning will occur when any single operator intermediate catheter is used. FIG. 10B illustrates schematically the inner (IP) and outer pathways (OP) for irrigation and aspiration which are formed by the catheter system of the present invention when a single operator intermediate catheter is used.

Another embodiment of an aspiration catheter suited for use as the intermediate catheter in the present invention is illustrated in FIGS. 11–13. The catheter 260 includes an adaptor 262, preferably a female luer adaptor, at its proximal end. The catheter 260 further includes an aspiration port 264 to which a source of negative pressure is attached. The aspiration catheter further comprises a long tubular body 266 having a distal end 268. The distal tip 268 can include a radiopaque marker to aid in locating the tip 268 during insertion into the patient, and is preferably soft to prevent damage to the patient's vasculature. The aspiration catheter is preferably about 145 cm in length, although this length can be varied as desired.

As seen in FIG. 12, the catheter body 266 is hollow, with an internal diameter ranging from about 0.020" to about 0.050". Preferably, the inner diameter is about 0.045". During insertion of the aspiration catheter 260, the proximal end of the inner catheter 270 is inserted into the distal end of the aspiration catheter 268, and the aspiration catheter 260 is slidably advanced over the inner catheter 270, which is positioned inside the hollow lumen 272 of the aspiration catheter 260. The position of the inner catheter 270 relative to the body of the aspiration catheter 266 is illustrated in FIG. 13, but of course, can vary. For this type of aspiration catheter 260, a very long inner catheter 270, generally around 300 cm in length, is used to facilitate the insertion of the aspiration catheter 260.

FIGS. 14–15 illustrate another embodiment of an aspiration catheter 250 suitable for use as an intermediate catheter in the present invention. This catheter 280 comprises an elongate shaft 282 with a lumen 284 for aspiration. At the distal end 288, a separate inner catheter lumen 286 is positioned adjacent the main aspiration lumen 284. Again, this lumen 286 provides a separate lumen, apart from the main lumen 284 of the catheter 280, for the insertion of the inner catheter. This inner catheter or guidewire lumen 286 can be as short as 5 cm, but can extend 30 cm or longer in a proximal direction. During delivery of the single operator aspiration catheter 280, the proximal end of the inner catheter is inserted into the distal end of the inner catheter lumen 286, and the lumen 286 is slidably advanced over the inner catheter. Only a short segment of the single operator aspiration catheter 280 rides over the inner catheter, and the inner catheter remains in the lumen 286 and does not enter the aspiration lumen 284 of the catheter 280. Again, the lumen 286 can have a slit (not shown) or weakened area in a side wall to facilitate insertion and/or removal of the inner catheter through the side wall of the lumen.

If desired, a rheolitic device such as the ANGIOJET thrombectomy catheter available from Possis Medical Inc., Minneapolis Minn. can be used. This device acts as both a therapy catheter and an irrigation/aspiration catheter. The device breaks up the thrombus or other occlusion and removes it. This eliminates the need to provide separate catheters for these functions. Thus, the term "aspiration catheter" includes rheolitic devices, thrombectomy devices and any device which creates an area of fluid turbulence and uses negative pressure to aspirate fluid and debris, and includes devices which create a venturi effect within the vessel.

Alternatively, a single catheter having two separate lumens can be used to provide both irrigation and aspiration. The dual lumen catheter can be configured to be over-the-wire, or of single operator design. Preferably, one lumen extends past the distal end of the catheter so that the opening of one lumen is spaced some distance apart from the opening of the second lumen. Thus, irrigation occurs some distance away from aspiration.

In another embodiment, a combined aspiration/therapy catheter can be used. For example, an angioplasty balloon can be attached to the distal end of an aspiration catheter. Alternatively, the aspiration catheter can be designed to deploy a stent within the occluded vessel, or the catheter could include an atherectomy device on its distal end. The aspiration and therapy devices are therefore delivered into the blood vessel together.

In the catheters of the present invention, the elongate catheter shaft must have sufficient structural integrity, or "stiffness," to permit the catheter to be pushed through the vasculature to distal arterial locations without buckling or undesirable bending of the body. It is also desirable, however, for the catheter body to be fairly flexible near its distal end, so that the tubular body may be navigated through tortuous blood vessel networks. Thus, the tubular body of the catheter can be formed from a polymer such as polyethylene, or PEBAX made to have variable stiffness along its length, with the proximal portion of the tubular body being less flexible than the distal portion of the body. Advantageously, a tubular body of this construction enables a user to more easily insert the tubular body into vascular networks difficult to access using conventional catheters of uniform stiffness. This is because the stiffer proximal portion provides the requisite structural integrity needed to advance the catheter without buckling, while the more flexible distal region is more easily advanced into and through tortuous blood vessel passageways.

Inner Catheter

As shown in FIGS. 16–17, the inner catheter apparatus 310 can generally be comprised of four communicating members including an elongated tubular member 314, a balloon member 316 and a core-wire, member 320 and a coil member 322. The catheter apparatus 310 is preferably provided with an outer coating of a lubricous material, such as TEFLON.

The body tubular member 314 of the catheter apparatus 310 is in the form of hypotubing and is provided with proximal and distal ends 314A and 314B and as well as an inner lumen 315 extending along the tubular member 314. The balloon member 316 is coaxially mounted on the distal end 314B of the tubular member 314 by suitable adhesives 319 at a proximal end 316A and a distal end 316B of the balloon member 316 as in the manner shown in FIG. 17. The core-wire member 320 of the catheter 310 may be comprised of a flexible wire 320. The flexible wire 320 is joined by soldering, crimping or brazing at a proximal end 320A of the flexible wire 320 to the distal end 314B of the tubular member 314 as in the manner show in FIG. 17.

Preferably, the proximal end 320A of the flexible wire 320 has a transverse cross sectional area substantially less than the smallest transverse cross-sectional area of the inner lumen 315 of the tubular member 314. In the preferred embodiment, the flexible wire 320 tapers in the distal end 320B to smaller diameters to provide greater flexibility to the flexible wire 320. However, the flexible wire may be in the form of a solid rod, ribbon or a helical coil or wire or combinations thereof.

As shown in FIG. 17, the distal end 320B of the flexible wire 320 is secured to a rounded plug 318 of solder or braze at the distal end 322B of the coil member 322. The coil member 322 of the catheter 310 may be comprised of a helical coil 322. The coil member 322 is coaxially disposed about the flexible wire 320, and is secured to the flexible wire 320 by soldering or brazing at about the proximal end 320A of the flexible wire 320 as in the manner shown in FIG. 17. The balloon member 316 is preferably a compliant balloon formed of a suitable elastic material such as a latex or the like. The flexible coil 322 is preferably formed of a radiopaque material such as platinum or gold. The flexible core-wire 320 and the tubular member 314 are preferably formed of a nickel-titanium alloy or stainless steel.

The catheters of the present invention are preferably provided with a coating on the outer surface, or on both the inner and outer surfaces. Suitable coatings include hydrophilic, hydrophobic and antithrombogenic coatings. Examples include heparin and TEFLON. These coatings can be applied using methods well known in the art.

Additional details relative to the catheters described above are found in U.S. patent application Ser. No. 08/813, 808, now abandoned, entitled ASPIRATION CATHETER, filed on Mar. 6, 1997, and U.S. Pat. Nos. 6,270,477, 5,868, 705 and 6,068,623, all of which are hereby incorporated by reference.

Fluid Mechanics of Irrigation/Aspiration

In order to understand the design criteria of the catheter system of the present invention, it is useful to have some understanding of the fluid mechanics of the system. The effect of the pressure differential between the irrigation and aspiration openings on the emboli containment chamber was first studied. It was confirmed that as the pressure differential increased, the flow rate in the chamber increased exponentially.

Some preliminary studies demonstrated that the fluid flow through the irrigation catheter into the chamber then out through the aspiration catheter could be represented by equations for fluid flow in pipes. The basic equation for incompressible fluid flow in a pipe is based on Bernoulli's equation for steady state flow of inviscid, incompressible fluids:

$$p_1 + 1/2\rho V_1^2 + \gamma Z_1 = p_2 + 1/2\rho V_2^2 + \gamma Z_2$$

where p=pressure, ρ=density, V=velocity, γ=specific weight, and Z=elevation. When fluid flows in a pipe or, in this case the irrigation/aspiration system within the containment chamber, the behavior of the fluid can be described by the equation:

$$\Delta p = K\rho V^2/2 \text{ let } K\rho/2 = k_2 \Delta p = k_2 V^2 \Delta p \, V^2$$

where K is the resistance coefficient and the fluid velocity V can be expressed in terms of fluid flow (Q) by the equation V=Q/A where A=cross sectional area. Therefore for a given irrigation/aspiration system K, A and ρ can be assumed to be constant, indicating that the square of the fluid velocity is proportional to the pressure differential between the irrigation and aspiration pressures.

The results of the initial testing clearly showed that the fluid flow through the system did behave as predicted and proved that as the change in pressure (Δp) increased the flow rate increased. The time required to remove emboli from the chamber with respect to the irrigation and aspiration pressures and the cross sectional area used for aspirating was also investigated. As expected, as the aspiration cross sectional area increased, there was a reduction in the time required to remove the emboli which was due to the corresponding fluid flow increase. The results showed that by increasing the initial Δp across the system, the flow rate increased as well, but the irrigation pressure had more effect on the flow rate than the aspiration pressure. The emboli removal was also affected by the flow rate with a shorter time being required for removal for a higher Δp and again, the higher irrigation pressure was the major factor.

There was some initial concern that pressure would build within the chamber if the configuration of the system or the change in pressure was not properly designed. However, in the studies performed, the pressure within the chamber ranged between −7.1 to 2 psig (gauge pressure where 0 psig=atmospheric pressure) depending on the main catheter internal diameter (ID) and the Δp across the system. These results indicate that over pressurization of the chamber is not an issue in this system.

Further investigation into the fluid mechanics in the emboli containment chamber was conducted as follows. A main catheter having an occlusion balloon on its distal end was first inserted into a 4 mm ID flexible polymer tube. A guidewire having a 4 mm inflatable occlusion balloon at its distal end was inserted through the main catheter and past the distal end of the main catheter so that a 100 mm chamber was created between the two balloons within the flexible tube. An irrigation catheter was then positioned just proximal of the guidewire balloon. The main and guidewire balloons were then inflated to isolate the chamber.

A pump was connected to an irrigation port on the irrigation catheter using a stop cock, and a pressure gauge was connected inline with the pump output line. A 60 cc syringe was connected to an aspiration port on the main catheter to provide aspiration pressure or vacuum. A vacuum/pressure gauge was connected inline with the aspiration line to the syringe. A 100 ml beaker of fluid (8.5 g/L sodium chloride solution or water) to be used in the test was then provided. The pump was operated until the chamber was filled with fluid and all the air was out of the irrigation and aspiration catheters.

A summary of the apparatus used in testing is shown below in Table 1:

TABLE 1

Test Apparatus Dimensional Breakdown

| | |
|---|---|
| Main Catheter ID/OD: | .065/.086 |
| Irrigation Catheter ID/OD: | .038/.046 |
| Asp. X-sectional Area: | .0017 in$^2$ |
| Chamber length: | 10 cm |

TABLE 1-continued

Test Apparatus Dimensional Breakdown

| | |
|---|---|
| Chamber ID: | .4 cm |
| Chamber Volume: | 1.3 cc |

With the input line to the pump in the filled beaker, the pump was operated and adjusted to the desired pressure. Twenty-five cc of fluid was measured and placed into an empty beaker, and the input line to the pump was placed into the beaker. The stop cock to the aspiration catheter was closed, and the plunger on the 60 cc syringe was pulled back until the desired vacuum was obtained. The pump was then turned on, and simultaneously, the stop cock to the aspiration port was opened and a timer was started. When the desired time had passed, the pump was turned off and the fluid remaining in the beaker and the fluid collected in the 60 cc syringe was measured.

A two level factorial design with two replications was used to determine the effect irrigation pressure and aspiration vacuum had on the flow rate through the system via the 4 mm×100 mm tubular chamber (see Table 2).

TABLE 2

Factors and levels

| Factor | Low Level | High Level |
|---|---|---|
| Irrigation Pressure | 5 psig | 30 psig |
| Aspiration Pressure | −10 in-Hg | −25 in-Hg |

The results of the testing are shown below in Tables 3 and 4.

TABLE 3

Flow Data Using a Saline Solution for Irrigation

| Initial* | Irr | Asp | δVin | | δVout | | δVin-δVout | | Time | | ASP Flow-Rate | |
|---|---|---|---|---|---|---|---|---|---|---|---|---|
| δP (psi) | Initial Press (psig) | Initial Press (in-Hg. gauge) | mean (cc) | stdev (cc) | mean (cc) | stdev (cc) | mean (cc) | stdev (cc) | mean (sec) | stdev (sec) | mean (cc/min) | stdev (cc/min) |
| 9.9 | 5 | −10 | 4.2 | .20 | 4.1 | .23 | .2 | .12 | 53.7 | 1.46 | 4.6 | .15 |
| 17.3 | 5 | −25 | 8.3 | .58 | 8.4 | .35 | −.1 | .23 | 54.8 | .37 | 9.2 | .33 |
| 19.9 | 15 | −10 | 9.1 | .12 | 8.8 | .20 | .3 | .31 | 53.2 | 1.04 | 9.9 | .41 |
| 27.3 | 15 | −25 | 10.5 | .46 | 8.4 | .53 | 2.1 | .42 | 55.6 | 2.45 | 9.1 | .65 |
| 34.9 | 30 | −10 | 10.1 | .12 | 9.3 | 9.27 | .8 | .40 | 53.7 | .58 | 10.4 | .36 |
| 42.3 | 30 | −25 | 10.2 | .40 | 9.1 | .61 | 1.1 | .23 | 53.6 | .58 | 10.2 | .57 |

TABLE 4

Flow Data Using a Water for Irrigation

| Initial* | Irr | Asp | δVin | | δVout | | δVin-δVout | | Time | | ASP Flow-Rate | |
|---|---|---|---|---|---|---|---|---|---|---|---|---|
| δP (psi) | Initial Press (psig) | Initial Press (in-Hg. gauge) | mean (cc) | stdev (cc) | mean (cc) | stdev (cc) | mean (cc) | stdev (cc) | mean (sec) | stdev (sec) | mean (cc/min) | stdev (cc/min) |
| 9.9 | 5 | −10 | 7.3 | .30 | 6.6 | .38 | .7 | .15 | 57.7 | 2.23 | 6.9 | .15 |
| 17.3 | 5 | −25 | 14.4 | 2.09 | 13.4 | 1.43 | 1.0 | 2.15 | 56.1 | .46 | 14.4 | 1.47 |

TABLE 4-continued

Flow Data Using a Water for Irrigation

| Initial* | Irr | Asp | δVin | | δVout | | δVin-δVout | | Time | | ASP Flow-Rate | |
|---|---|---|---|---|---|---|---|---|---|---|---|---|
| δP (psi) | Initial Press (psig) | Initial Press (in-Hg. gauge) | mean (cc) | stdev (cc) | mean (cc) | stdev (cc) | mean (cc) | stdev (cc) | mean (sec) | stdev (sec) | mean (cc/min) | stdev (cc/min) |
| 19.9 | 15 | −10 | 12.1 | 4.22 | 9.3 | .58 | 2.8 | 3.64 | 56.0 | .57 | 10.0 | .56 |
| 27.3 | 15 | −25 | 10.5 | .50 | 9.9 | .61 | .6 | 53 | 54.6 | 2.81 | 10.9 | .78 |
| 34.9 | 30 | −10 | 10.9 | 1.01 | 10.1 | .50 | .7 | .76 | 55.5 | 3.41 | 11.0 | .15 |
| 42.3 | 30 | −25 | 9.8 | .35 | 10.0 | .20 | −2 | .20 | 53.1 | .99 | 11.3 | .15 |

*Pressure equalization after max 45 sec. As δP increases, the time to equalize increases
δP is the pressure differential between the irrigation bag and the vacuum in the aspiration syringe
V = volume and n = 3 unless otherwise noted The irrigation pressure was varied between 5 and 30 psig with the aspiration pressure varying between −10 and −25 in-Hg. The results show that there was little difference between the use of the saline solution and the use of water. The lowest flow rate of 4.6 cc/min was obtained for a 5 psi irrigation pressure and a −10 in-Hg aspiration pressure (δp=9.9 psi). The highest flow rates were obtained when a 30 psi irrigation pressure was used with rates of 10.4 and 10.2 cc/min for an aspiration pressure of −10 (δp=34.9 psi) and −25 in-Hg (δp=42.3 psi) respectively.

The results of this two level factorial design supported the results obtained in earlier studies: that as the δp across the system increases, the flow rate increases exponentially.

Figure 19:
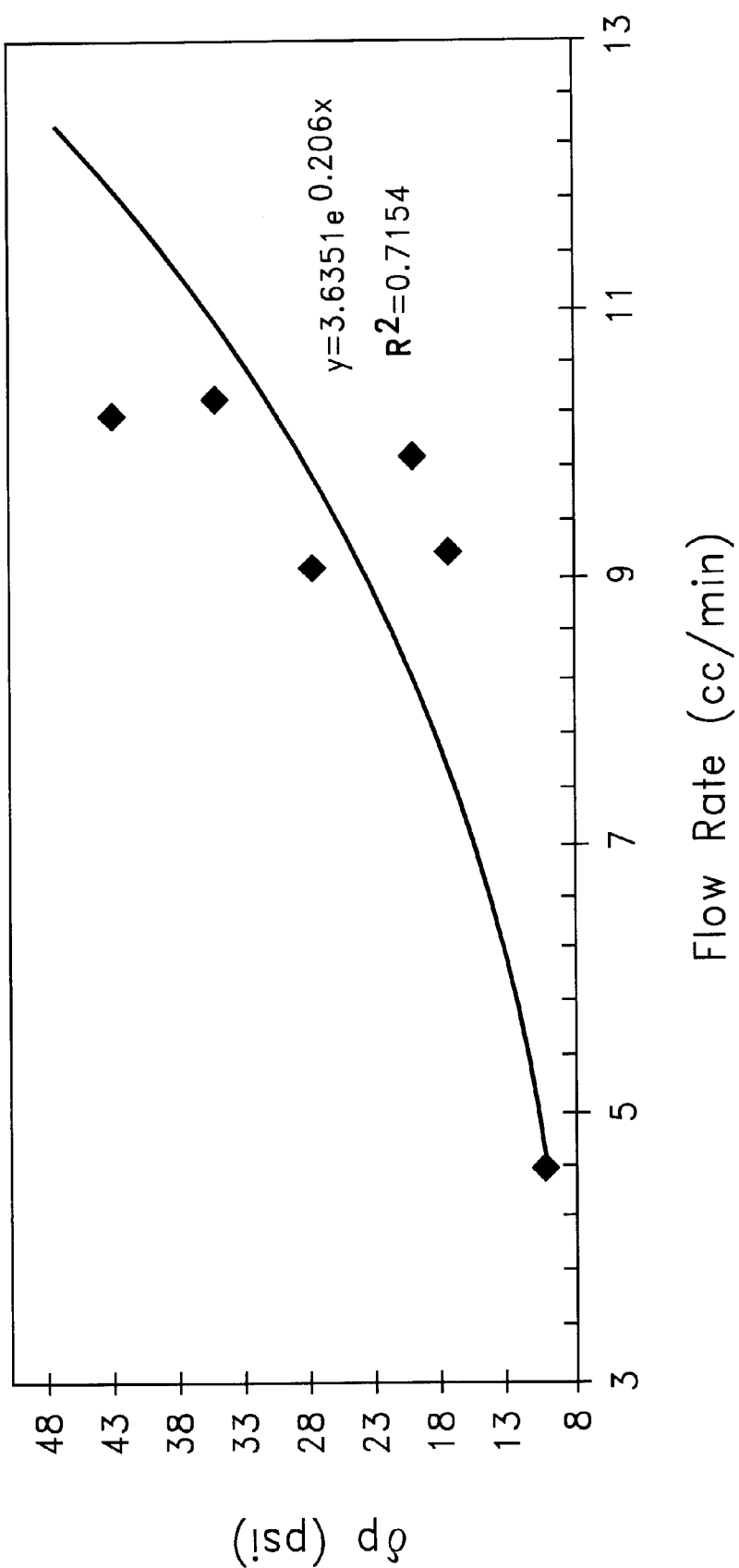
FIG. 19 is a graph illustrating the exponential trend of fluid flow versus pressure in the emboli containment chamber.

The results were consistent with Bernoulli's equations for flow in a tube in that the fluid velocity is proportional to the square root of the pressure differential between the two points assuming a constant fluid density and losses. When the flow rate was plotted against δp an exponential trend with an $R^2=0.7154$, the results support the proportional relation between pressure and the fluid flow rate expressed in equation 2 (see FIG. 19).

Analysis of the data produced an extremely significant model with an adjust $R^2=0.994$ (see Table 5). Each of the main factors as well as the interaction between the irrigation and aspiration pressure were highly significant with a p<0.0000.

TABLE 5

Data Analysis and Model for Flow Rate (solution: saline)

| Adjusted $R^2$ | | | .994 | |
|---|---|---|---|---|
| Standard Error | | | .227 | |
| Mean Abs. Error | | | .1278 | |
| | Coefficient | Error | Factor* | p-value |
| Flow Rate (cc/min) = | 8.6 | ∀ .0654 | | |
| | 3.367 | ∀ .1309 | Irrigation | .0000 |
| | −2.2 | ∀ .1309 | Aspiration | .0000 |
| | 2.37 | ∀ .1309 | Irr* Asp | .0000 |

*Use coded values between −1 and 1 to determine predicted flow rates

Figure 20:
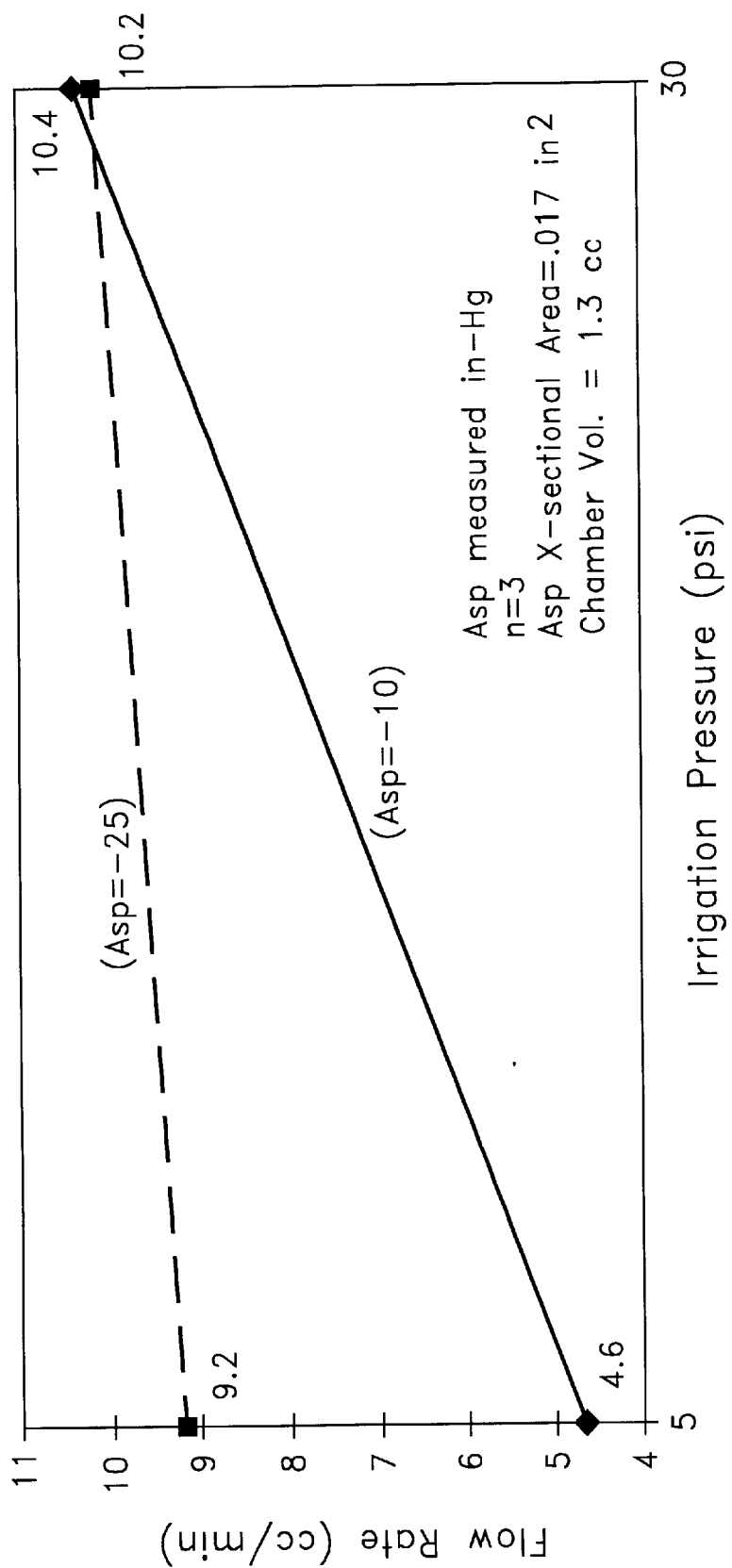
FIG. 20 is a graph illustrating the effect of irrigation and aspiration pressures on flow rate within the emboli containment chamber.

The analysis of the interaction between the irrigation and aspiration pressure showed that by using a lower aspiration pressure of −25 in-Hg the effect of the irrigation pressure can be minimized (see FIG. 20). The increase in the flow rate between 5 and 30 psig was 1.0 cc/min for an aspiration pressure of −25 in-Hg, whereas the increase was significantly higher, 5.6 cc/min, when an aspiration pressure of −10 in-Hg was used. Another advantage of using the lower aspiration pressure was that it took longer for the pressure to equalize as measured by the aspiration pressure gauge thus a higher flow rate was sustained over a longer period of time.

The tubular chamber used in this study was 4 mm×100 mm which contained a volume of 1.3 cc; therefore for the worst case flow rate of 4.6 cc/min (IP=5 psig, AP=−10 in-Hg) the fluid is exchanged approximately 3.5 times taking approximately 17 seconds for each exchange. The fluid collection in one minute is 9.2 cc for an IP=5 psig and an AP=−25 in-Hg, which would flush the 1.3 cc chamber in approximately 7.5 seconds or 8 times per minute.

This understanding of the fluid mechanics inside the emboli containment chamber resulting from the testing described above lead to the development of the method of the present invention, which provides efficient irrigation and aspiration for removal of emboli and debris inside the body following treatment of an occluded vessel.

Emboli Containment Methods of the Present Invention

The operation and use of the emboli containment system utilizing the catheters of the present invention for treating occluded vessels will now be described in connection with an occlusion formed by a stenosis in a carotid artery, as illustrated in FIGS. 18A–H. It should be noted that this application is merely exemplary, and that the method of the present invention can be used in other blood vessels in the body as well. The word "proximal" as used herein refers to the portion of the catheter closest to the end which remains outside the patient's body, while "distal" refers to the portion closest to the end which is inserted into the body.

A guiding catheter (not shown) is first introduced into the patient's vasculature through an incision in the femoral artery in the patient's groin. The guide catheter is advanced through the artery into the aorta of the heart of the patient and into the ostium of the carotid artery to be treated, where it remains throughout the procedure if needed. Fluoroscopy is typically used to guide the catheter and other devices to the desired location within the patient. The devices are typically marked with radiopaque markings to facilitate visualization of the insertion and positioning of the devices.

Figure 18C:
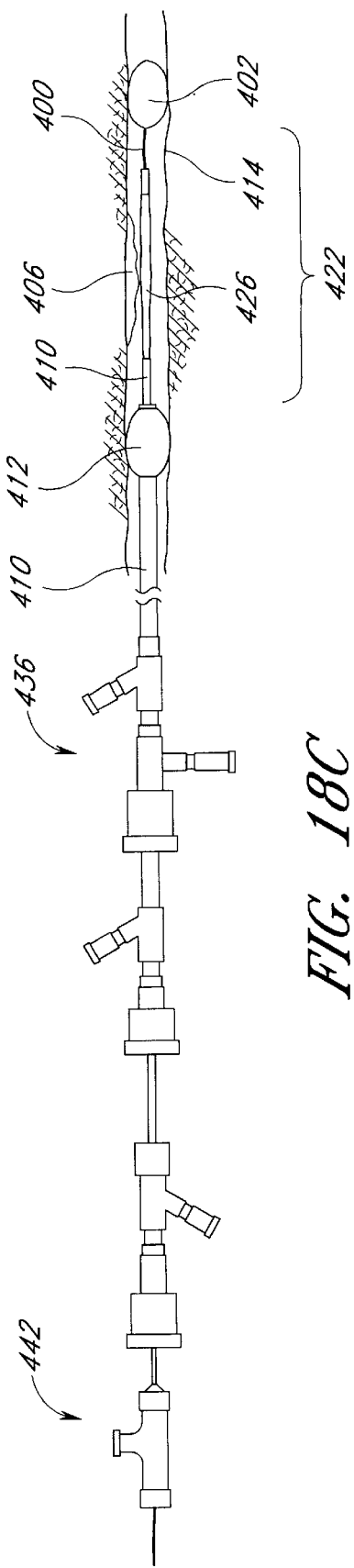

Referring now to FIG. 18A, a main catheter 410 having a distal attached occlusive device 412, in this example an inflatable balloon, is advanced into the ostium of the carotid artery and into the lumen 418 of the vessel 414. The main catheter 410 with the occlusive device 412 thereon is advanced until the device 412 is just proximal to the stenosis 406. The device is activated, i.e. the balloon 412 is then inflated, to occlude the vessel 414. The inner catheter, in this example a guidewire 400, having an occlusive device 402, in this example an inflatable balloon, at its distal end 404 is next delivered through the main catheter 410. The occlusive device 402 is positioned just distal to the occlusion 406. The occlusive device is activated, i.e., the balloon 402 is inflated to create an isolated chamber within the vessel which surrounds the occlusion. The balloons 402, 412 are each progressively inflated until they engage the side wall of the vessel 414 to occlude the lumen 418. Preferably, the distance between the proximal end of the occlusive device on the guidewire 404 and the distal tip of the occlusive device on the main catheter 416 should be approximately 5–10 cm. Advantageously, the present invention allows for the creation of a treatment and containment chamber whose length can be easily adjusted to isolate a specific area within a blood vessel. As soon as both balloons 402, 412 are inflated, a working space 422 is provided between the balloons 402, 412, so that therapeutic procedures can be undertaken to remove or reduce the occlusion 406 in the space between the balloons 422, without risk of unwanted particles or emboli escaping into the blood stream. The inner catheter 400 and the main catheter 410 with their attached distal occlusive devices 402, 412 are therefore used to create a chamber 422 surrounding the occlusion 406, and act to contain the emboli and debris 424 resulting from the treatment of the occlusion 406 as illustrated in FIG. 18C.

Alternatively, a guide catheter or angiography catheter can first be delivered to the site of the occlusion. The inner catheter is inserted through the guide or angiography catheter, and positioned within the patient. The guide or angiography catheter is removed, and the main catheter is inserted over the inner catheter into position proximal to the occlusion. The occlusive device at the distal end of the main catheter is activated, the occlusive device on the inner catheter is put into position distal to the occlusion and activated, and the procedure continues as described above.

Alternatively, the main catheter can be delivered directly to a position just proximal to the occlusion, without use of a guide or angiography catheter. The inner catheter is then delivered through the main catheter as described above.

In another alternative embodiment of the present invention, the inner catheter can be delivered first through the guide catheter. The occlusive device on the distal end of the inner catheter is positioned distal to the occlusion. The main catheter is introduced over the inner catheter and advanced into the ostium of the carotid artery and into the lumen of the vessel. The main catheter is advanced until the balloon is just proximal to the occlusion. The intermediate catheter is then delivered into the chamber to provide appropriate therapy. The occlusive devices on the distal ends of the inner and main catheters are activated, to create a treatment and isolation chamber surrounding the occlusion. This method can be used when the physician determines that the risk of crossing the occlusion prior to activation of the proximal occlusive device is minimal.

Referring now to FIG. 18B, once the chamber has been created around the occlusion, an intermediate catheter 420 is delivered to the site of the occlusion 406. In the example illustrated in FIGS. 18A–F, the intermediate catheter 420 is a therapy catheter having an angioplasty balloon on its distal end. The intermediate catheter 420 is delivered to the site of the occlusion 406 as shown in FIG. 18B.

The term "therapy catheter" is meant to include any of a number of known devices used to treat an occluded vessel. For example, a catheter carrying an inflatable or mechanically activated balloon for use in balloon angioplasty, as is used in this example, can be delivered to dilate the stenosis. Thermal balloon angioplasty includes the use of heat to "mold" the vessel to the size and shape of the angioplasty balloon. Similarly, an intravascular stent can be delivered via a balloon catheter and deployed at the site of the stenosis to keep the vessel open. Cutting, shaving, scraping, or pulverizing devices can be delivered to excise the stenosis in a procedure known as atherectomy. A laser or ultrasound device can also be delivered and used to ablate plaque within the vessel. Various types of rheolitic devices could be used. Various thrombolytic or other types of drugs can be delivered locally in high concentrations to the site of the occlusion. It is also possible to deliver various chemical substances or enzymes via a catheter to the site of the occlusion to dissolve the obstruction. A combined aspiration and therapy catheter can also be used. The term "therapy catheter" encompasses these and other similar devices.

Figure 18D:
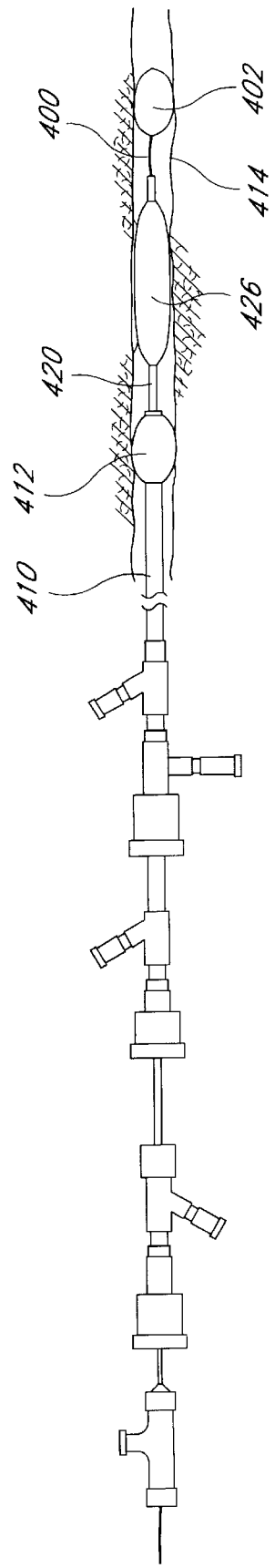

Referring now to FIG. 18D, after the balloons 402 and 412 are properly inflated, and the therapy catheter 420 in place, therapy begins. For emboli containment systems featuring balloon dilatation treatment, it is desired to compress the plaque or material forming the 406 to provide a larger passageway through the vessel. Thus, a balloon angioplasty catheter 420 is positioned such that the distal end with the balloon 426 thereon is at the site of the occlusion 406. When the balloon 426 has been properly positioned within the 406, the balloon 426 is inflated with a suitable inflation medium, as for example a radiopaque liquid. The angioplasty balloon 426 can be inflated to the desired pressure to cause compression of the plaque of the occlusion 406 against the sidewall of lumen 414 by the application of appropriate inflation pressure, as shown in FIG. 18D. As in conventional angioplasty procedures, the balloon 426 can be formed of a non-elastic relatively non-compliant material so that appropriate pressures, such as 10–15 atmospheres, can be created within the balloon to apply compressive forces to the vessel 414 without danger of rupturing the vessel 414. It should be appreciated that the non-elastic capabilities can also be achieved by a composite elastic material.

After appropriate therapy has been performed and the occlusion 406 has been removed or lessened using any of the methods and apparatus described above, the therapy balloon 426 is deflated as illustrated in FIG. 18E. A source of irrigation fluid (not shown) is connected to the adaptor 434 located at the proximal end of the therapy catheter 420, and a source of aspiration pressure (not shown) is connected to an adaptor 436 located at the proximal end of the main catheter 410, as illustrated in FIG. 18F. Preferably, the source of irrigation fluid is a bag of normal saline, typically used in intravenous infusion. The source of aspiration pressure is preferably a syringe. After the source of irrigation and aspiration are connected, irrigation and aspiration are begun. Irrigation fluid is provided through the inner pathway between the therapy catheter 420 and the guidewire 400, while aspiration is provided through the outer pathway between the therapy catheter 420 and the main catheter 410 as shown by the small arrows in FIG. 18F. Of course it is to be understood that irrigation fluid could be provided through the outer pathway while aspiration is provided through the inner pathway. In either case, suitable pressures are provided to ensure that the change in pressure inside the chamber does not damage the vessel. The change in pressure as fluid flows into and out of the chamber should not exceed about 50 psi. Suitable pressures range from approximately −10 to −30 in-Hg aspiration pressure, and about 5 to 30 psig irrigation pressure. Note that these pressures are measured at the proximal end of the catheters.

In an alternative embodiment not shown, after therapy has been performed to remove or reduce the occlusion the therapy catheter is removed from the emboli containment system, and an irrigation catheter is delivered to the emboli containment chamber. The irrigation catheter is inserted through the main catheter lumen. The main lumen of the irrigation catheter can ride over the inner catheter, or the inner catheter can be positioned in a separate lumen adjacent to the main lumen. The distal end of the irrigation catheter is positioned just proximal the distal occlusion balloon, preferably approximately 1–2 cm from the balloon. As noted above, the irrigation and main catheter are sized such that the irrigation catheter can pass through the main catheter lumen and the annulus or outer pathway between the main catheter lumen and the irrigation catheter is large enough to allow aspiration of the blood and debris through it. Irrigation fluid is provided through the inner pathway between the inner catheter and the irrigation catheter. Alternatively, an aspiration catheter, a combined irrigation/aspiration catheter, or similar debris removing device such as a rheolitic device, can be used as the intermediate catheter. In this embodiment of the invention, the aspiration catheter is delivered in the same manner as described above for the irrigation catheter. Aspiration then occurs through the inner pathway, while irrigation is provided through the outer pathway.

Once the desired catheters are properly positioned, irrigation and aspiration are performed. The irrigation fluid and aspiration pressure are delivered in such a way as to ensure that the change of pressure within the chamber is below about 50 psi to avoid damaging the vessel. The irrigation fluid, preferably normal saline solution, is preferably delivered at a pressure of from about 5 psi to about 50 psi; 5 psi is preferred. The aspiration pressure is preferably between about −5 and −30 in-Hg, and more preferably is about −20 in-Hg. Again, these pressures are measured from at the proximal end of the catheters. The irrigation and aspiration can be delivered simultaneously, continuously, or delivery can be pulsed, or one can be delivered continuously while the other is delivered in a pulsed fashion. The user can determine the best method of delivery to provide optimized flow, turbulence, and clearance within the chamber.

Referring again to FIG. 18F, it is preferable that the inflation pressure within the distal occlusion balloon 402 is maintained at a level greater than the pressure in the chamber and the jet created by irrigation to avoid the leakage of fluid and debris past the distal occlusion balloon 402. Similarly, the inflation pressure in the proximal occlusion balloon 412 should be maintained at a level greater than the pressure in the chamber and the aspiration pulsation to avoid having fluid aspirated from behind the balloon 412 and possibly aspirating the balloon 412 itself. Again, the irrigation and aspiration pressures provided are such that the change in pressure during fluid flow into and out of the vessel does not damage the vessel. The change in pressure is preferably no greater than about 50 psi.

In another embodiment of the present invention, after the therapy catheter is removed, the aspiration catheter is delivered such that its distal end is positioned approximately 1–2 cm from the distal occlusive device. The proximal occlusive device is then deactivated, to allow blood flow into the chamber. This blood flow is used as irrigation flow. The blood, acting as irrigation fluid, is aspirated together with particles and debris through the aspiration catheter. This eliminates the need for a separate source of irrigation fluid. In this embodiment, it is preferred that the blood flow rate in the vessel is greater than about 100 cc/min, and flow rates of 60–80 cc/min are preferred. This method is illustrated in FIG. 18H.

Figure 18G:
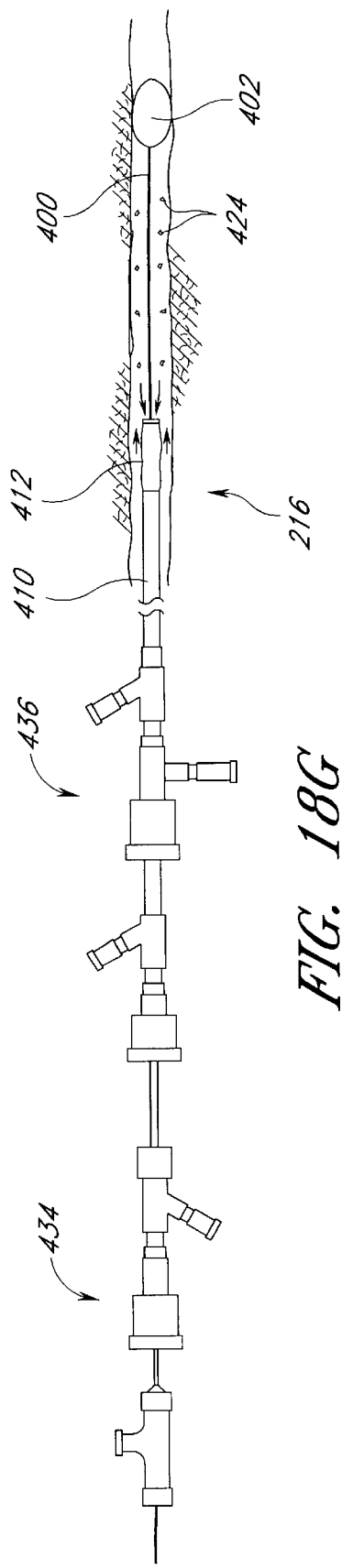
Figure 18H:
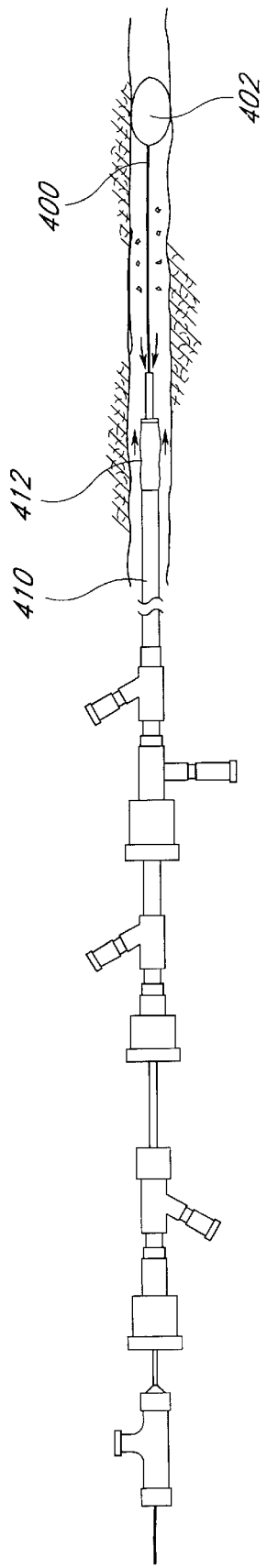

In yet another embodiment, illustrated in FIG. 18G, after the therapy catheter is removed, the proximal occlusive device is deactivated, allowing blood flow into the chamber. The blood, acting as irrigation fluid, is aspirated together with particles and debris through the opening in the main catheter. This eliminates the need for a separate aspiration catheter and a separate source of irrigation fluid, thereby reducing the time necessary to complete the procedure.

Aspiration and irrigation are continued until particles and debris 424 are removed from the chamber 422, then the irrigation, aspiration, or the therapy catheter 420, is removed. First the distal 402 and then the proximal 412 occlusion balloons are deflated, and the guidewire 400 and main catheter 410 are removed. Finally, the guide catheter is removed, and the incision in the patient's femoral artery is closed.

Alternative Emboli Removal Methods

FIGS. 21–24 illustrate a main catheter 651 which is utilized as a part of an apparatus according to another embodiment. The main catheter 651 consists of a flexible elongate tubular member 652 formed of a suitable material such as plastic of the type hereinbefore described and has proximal and distal extremities 653 and 654. The tubular flexible elongate tubular member 652 can be of various sizes as for example for a saphenous vein graft catheter it can be 8 to 9.5 French in balloon profile with a length ranging from 80 cm to 120 cm. The flexible elongate tubular member 652 can be formed of a suitable material such as PEBAX, Nylon, Hytrel, polyurethane or polyethylene. A flexible braid 656 (see FIGS. 22, 23 and 24) formed of a suitable material such as stainless steel is embedded within the wall of the flexible elongate tubular member 652 as shown and extends from the proximal extremity 653 to the distal extremity 654. The braid 656 can be formed of a suitable stainless steel such as a wire or ribbon having a thickness of 0.001". The braid 656 provides additional torquability and also inhibits the kinking of the flexible elongate tubular member 652 when it must extend over a tight radius. The flexible elongate tubular member 652 is provided with a large central lumen 657 having a suitable diameter such as 0.065 or greater" extending from the proximal extremity to the distal extremity.

If it is desired to provide a flexible elongate member 652 which has a greater flexibility at the distal extremity, a different material can be used in the distal extremity 654. For example, the distal most 5–15 centimeters can be formed of a material such as PEBAX having a Shore D hardness of 35–50 with the remainder of the flexible elongate member 652 having a Shore D hardness of 65–75.

A supplemental flexible elongate tubular member 661 is provided which has incorporated therein a balloon inflation lumen 662. The supplemental flexible elongate tubular member 661 can be of a suitable size as for example an I.D. of 0.014" and an O.D. of 0.018" and formed of a suitable material such as a polyimide. The supplemental flexible elongate tubular member has a length which is almost as long as the flexible elongate tubular member 652 and overlies the outside wall of the flexible elongate tubular member 652 and extends from the proximal extremity to near the distal extremity as shown in FIGS. 21 and 24. A tube 663 of a suitable material such as Pebax extends over the length of the polyimide tubing 661 and is secured to the flexible elongate tubular member 652 by a shrink tube 666 extending from the proximal extremity 653 to the distal extremity 654, after which the shrink tube 663 is subjected to heat. The shrink tube 666 is then subjected to a hot melt process of a temperature around 350° F. for a period of time until the Pebax tube 663 melts, after which the shrink tubing 666 can be stripped off so that there remains a relatively uniform mass formed of Pebax that surrounds the braid 657 and the polyimide tube 661 which forms the supplemental flexible elongate tubular member 661. The polyimide tube which forms the supplemental flexible elongate tubular member 661 thus provides an inflation lumen 667 extending from the proximal extremity and to the distal extremity and opens through an opening 668 into the interior of an occlusion balloon 669 which is bonded to and coaxially mounted on the distal extremity of the flexible elongate member 652 in the manner shown in FIG. 24. The polyimide tubing is provided to give the balloon inflation lumen shaft 361 greater strength than that which is provided by the Pebax itself.

As can be seen from FIG. 24, the supplemental flexible elongate tubular member 661 is terminated short of the distalmost extremity of the flexible elongate tubular member 652 by approximately 1 cm. The occlusion balloon 669 is formed of various compliant or non-compliant materials. Suitable compliant materials include elastomers such as C-Flex latex, silicones and polyurethanes. Suitable non-compliant materials would be polyethylene, PET and Nylon. A composite material can also be used such as a combination of PET and an elastomer. The occlusion balloon 669 should have a strength so that it can readily accommodate any pressure of one atmosphere and as high as four atmospheres, or approximately 60 psi. The occlusion balloon 669 is cylindrical and is provided with proximal and distal extremities 671 and 672 which are secured by a suitable medical grade adhesive. Alternatively, fuse bonding may be used. Thus a seal 673 formed of this adhesive bonds the proximal extremity 671 of the occlusion balloon 669 over the outer surface of the distal extremity of the flexible elongate tubular member 652 and the supplemental flexible elongate tubular member 661. Similarly, a seal 674 bonds the distal extremity 672 to the distal extremity of the flexible elongate tubular member 652 to provide an air-tight space within the balloon accessible through the opening 668. A soft cylindrical tip 676 formed of suitable material such as Pebax is bonded to the distal extremity of the flexible elongate tubular member 652 and is provided with a rounded surface 677 which extends forwardly and has a passage 678 therein in communication with the lumen 657 and the flexible elongate tubular member 652. A cylindrical radiopaque marker 681 formed of a suitable material such as platinum, platinum-iridium or gold is mounted on the distal extremity of the flexible elongate tubular member 652 in a position so it is substantially equidistant of the ends of the occlusion balloon 669.

A main adapter or fitting 686 formed of a suitable material such as plastic is mounted on the proximal extremity 653 of the flexible elongate tubular member 652. It is provided with a first luer fitting 687 which provides a balloon inflation port 688 in communication with the balloon inflation lumen 662. It is also provided with another Luer fitting 689 which is provided with an aspiration port 691 in communication with the main central lumen 657. The main adapter 686 is also provided with a Tuohy-Borst fitting 692 which is in communication with the central lumen 657. The Tuohy-Borst fitting 692 is adapted to receive therapeutic devices, as for example a balloon-on-a-wire device as hereinafter described and is adapted to form a liquid-tight seal therewith by an o-ring 693.

A balloon-on-a-wire device 701 incorporating the present invention is shown in FIGS. 25 and 26. The device 701 consists of a guide wire 702 formed of a suitable material such as stainless steel and having a suitable diameter as for example ranging from 0.010" to 0.032" but preferably a diameter ranging from 0.014" to 0.018". It is preferable that the guide wire 702 be formed of a nickel titanium alloy typically called Nitinol which has the advantage that it is more flexible and has greater kink resistance characteristics than another suitable material such as stainless steel.

It has a suitable length as for example 150 cm. The guide wire 702 is provided with proximal and distal extremities 703 and 704 and is provided with a central lumen 706 extending from the proximal extremity to the distal extremity. The lumen can be of a suitable size as for example 0.010" I.D. for an 0.014" O.D. guide wire.

An occlusion balloon 711 is coaxially mounted on the distal extremity 704 of the guide wire 702. The occlusion balloon 711 is preferably formed of the same material as the occlusion balloon 669 on the main catheter 651. The occlusion balloon 711 has proximal and distal extremities 712 and 713. A tube 716 formed of a suitable material such as a polyimide is disposed within the occlusion balloon 711 and has a bore 717 extending therethrough which is sized so that it is slightly larger than the outside diameter of the guide wire 702 so that its proximal extremity can be slipped over the distal extremity 704 of the guide wire 702 and then bonded thereto by suitable means such as an adhesive 718. A plurality of circumferentially spaced apart radially extending inflation holes 719 are provided in the proximal extremity of the tube 716 and are in alignment with similarly spaced holes 721 provided in the distal extremity 704 of the guide wire 702 so that they are in communication with the central lumen 706 of the guide wire 702. The inflation holes 719 as shown are in communication with the interior of the occlusion balloon 711 so that fluid passing from the passage 706 can be utilized for inflating the occlusion balloon 711.

A solid core wire 723 formed of a suitable material such as stainless steel is provided with a proximal tapered extremity 724. The core wire 723 is sized so it is adapted to fit within the lumen 706 of the guide wire 702 and is secured therein by suitable means such as an adhesive 726 or alternatively a weld. The core wire 723 has a tapered portion 723a which commences at the proximal extremity 724 and which is tapered so that the cross-sectional diameter progressively decreases to the distal extremity of the occlusion balloon 711. The core wire 723 is also provided with additional portions 723b and 723c which can be of substantially constant diameter as for example 0.003". The portion 723 is folded over with respect to the portion 723b so that the portions 723b and 723c lie in a plane to facilitate shaping of the distal extremity of the guide wire 702 during use of the same. The core wire 723 is provided with a distal extremity 727 in which a bend 728 is formed between the two portions 723b and 723c. The bend 728 is secured within a hemispherical solder bump or protrusion 729 which is carried by the distal extremity of a coil 731 formed of a suitable radiopaque material such as platinum or a platinum alloy. The platinum coil 731 can have a suitable outside diameter as for example 0.014" corresponding to the diameter of the guide wire 702 and can have a suitable length ranging from 1 to 3 cm. The proximal extremity of the coil 731 is secured to the distal extremity of the polyimide tube 716 by suitable means such as an adhesive 732 which can be the same adhesive or a different adhesive 733 utilized for securing the distal extremity 713 of the balloon to the polyimide tube 716 to form a fluid-tight seal between the distal extremity of the occlusion balloon 711 and the distal extremity of the polyimide 716. From this construction it can be seen that the portions 723b and 723c of the core wire 723 in addition to serving as a shaping ribbon are also utilized as a safety ribbon to ensure that the tip 728 and the spring 731 cannot be separated from the guide wire 702. The proximal extremity 712 of the balloon 711 is also secured to the proximal extremity of the polyimide tube 716 and also to the distal extremity 704 of the guide wire 702 to form a fluid-tight seal with respect to the occlusion balloon 711 so that the occlusion balloon 711 can be inflated and deflated through the inflation holes 719 and 721.

Alternative constructions for the distal extremity of the core wire 723 are shown in FIGS. 28 and 29. In FIG. 28 it can be seen that the portions 723b and 723c have been twisted to in effect provide a twisted pair serving as a safety ribbon and as a shaping ribbon. In the embodiment shown in FIG. 29, the core wire 736 is provided with a tapered portion 736a which is the same as the tapered portions of 723a hereinbefore described. However, the core wire 736 has been provided with a distal portion 736b which has been flattened to a suitable thickness as for example a width of 0.006" and a thickness of 0.003" and then twisted to form a helix as shown in which the distal extremity is embedded within the solder 729. Such a helix 736 can serve as a safety ribbon and also can be shaped to some extent.

A removable inflation fitting 741 or valve attachment 741 is mounted on the proximal extremity of the guide wire 702 and forms a part of the balloon-on-a-wire device 701. The fitting or attachment 741 is formed of a suitable material such as a polycarbonate and is provided with a central bore 742. The attachment or fitting is slid externally over the proximal extremity 703 of the guide wire 702. Means is provided for forming a fluid-tight seal between the proximal extremity 703 of the guide wire 702 and a body 743 of the fitting 741 and consists of an o-ring 746 (see FIG. 30) seated in a well 747. A thumb screw 748 is threadedly mounted on the body 743 and is provided with an inwardly extending circular protrusion 749 that is adapted to engage the o-ring 746 and to compress the same to form a fluid-tight seal when the protrusion 749 is moved inwardly toward the o-ring 746 as the thumb screw 748 is rotated in a clockwise direction. The o-ring 746 decompresses or springs back when released upon rotation of the thumb screw 748 in a counterclockwise direction so that the fitting 741 can be removed from the distal extremity 703 of the guide wire 702. The body 742 also includes a Luer fitting 751 which provides an inflation port 752 that is in communication with the bore 742 in the body 743 and which is also in communication with the open proximal extremity of the guide wire 702 and the lumen 706 therein.

Means is provided for plugging the bore 706 when the removable attachment or fitting 741 is removed and consists of a plug mandrel 756 formed of a suitable material such as 0.014" stainless steel solid rod. It is necessary that this rod have a diameter which is greater than the diameter of the lumen 706 and the guide wire 702. The plug mandrel 756 is provided with a progressive portion 756a that tapers down from as, for example from 0.014" to a suitable diameter as for example 0.008" to a cylindrical portion 756b.

Means is provided for forming a fluid-tight seal between the plug mandrel 756 which forms a plug mandrel and the body 743 of the attachment or fitting 741 and consists of an o-ring 766 providing suitable sealing means seated within a well 762 provided in the body 743. A thumb screw 763 threadedly engages the body 743 and is provided with a cylindrical protrusion 764 which engages the o-ring and compresses it to form a fluid-tight seal with respect to the plug mandrel 756 by rotation in a clockwise direction of the thumb screw 763. The plug mandrel 756 can be released by a counterclockwise rotation of the thumb screw 763 permitting decompression of the o-ring 761.

An irrigation catheter 766 incorporating the present invention is shown in FIG. 31 and consists of a flexible elongate tube 767 formed of a suitable material such as polyethylene, PEBAX, Hytrel or Teflon having a suitable size as for example an outside diameter of 0.066" and an inside diameter of 0.058" and having a length of approximately 150 cm. A lumen 768 is provided therein and extends from the proximal extremity to the distal extremity and is in communication with an adapter 769 provided on the proximal extremity of the tube 767. The adapter 769 is provided with a body 770 formed of a suitable material such as plastic and is provided with a bore 771 extending therethrough. The adapter 769 is provided with a side arm 772 which carries a conventional Luer-type connection and provides an irrigation port 773 in communication with the bore 771. A thumb screw 774 threadedly mounted on the body 770 carries a cylindrical protrusion 776 adapted to compress an o-ring 777 carried by the body 770 into engagement with a therapeutic catheter of the type hereinafter described. A radiopaque tip marker 778 of a suitable type, as for example one formed as a platinum-iridium band 778 is provided on the distal extremity of the flexible elongate element 767 to facilitate positioning of the irrigation catheter as hereinafter described.

Operation of the apparatus shown in FIGS. 21 through 31 in performing the method of the present invention for treating occluded vessels may now be briefly described as follows utilizing the cartoons which are shown in FIGS. 32–38. Let it be assumed that it is desired to treat a vessel 781 in the human body as for example a saphenous vein graft having at least a partial occlusion or stenosis 782 which is formed by plaque in the vessel. The main catheter 651 is introduced into the body through a conventional procedure such as for example by making an incision into the femoral artery in a leg of the patient.

Thereafter the main catheter 651 can be introduced into the femoral artery by use of a large conventional guiding catheter because the main catheter 651 is of a relatively large size, as for example 8 to 9.5 French. In order to eliminate the need for such a large guiding catheter, a smaller conventional guiding catheter 786 of the type shown in FIG. 32 can be utilized which can be introduced through the main catheter 651. Utilizing such a catheter, the main catheter 651 can be inserted independently through a conventional sheath (not shown) in the femoral artery and thereafter the guiding catheter 786 is introduced through the main catheter 651 so that its distal extremity 789 is in the vessel. Alternatively, the guiding catheter 786 can be deployed into the main catheter 651 and the guiding catheter 786 introduced at the same time into the femoral artery.

The guiding catheter 786 is conventional and thus will not be described in detail. It consists of a flexible elongate tubular member 787 (see FIG. 32) formed of a suitable material such as plastic having proximal and distal extremities 788 and 789. The distal extremity 789 is provided with a preformed bend as shown. An adapter 792 is mounted on the proximal extremity 788 and consists of a body 793 in the form a wye in which the central leg 794 is provided with a flow passage (not shown) therein in communication with the central lumen (not shown) extending from the proximal extremity 788 to the distal extremity 789 of the flexible elongate tubular member 787. The body 793 is provided with a side leg 796 which also is in communication with a lumen (not shown) extending from the proximal extremity 788 to the distal extremity 789. A knob 797 carrying an o-ring (not shown) secures the adapter 792 to the proximal extremity 788 with a fluid-tight seal. Another knob 798 is provided which is carried by the central leg 794 of the body 793 and is provided with an o-ring (not shown) which can be moved to close the flow passage in the central leg 794, or alternatively it can be opened to receive a guide wire which can be utilized for advancing the guide catheter 786 if that be necessary and then forming a fluid-tight seal with respect to the guide wire.

Assuming that the guiding catheter 786 has been inserted into the main catheter 651 before insertion of the main catheter 651 into the femoral artery, both catheters can be inserted in unison while advancing the distal extremity of the guide catheter 786 so that it precedes the distal extremity of the main catheter 651 and serves to guide the main catheter 651 into the vessel of interest, as for example the vessel 781 having the stenosis 782 therein. The main catheter 651 is then advanced so that its distal extremity is at the proximal side of the stenosis 782. By way of example, the main catheter 651 can be advanced through the aortic arch of the heart and thence into a saphenous vein graft so that the occlusion balloon 669 on its distal extremity is positioned proximal of the stenosis 782. As soon as this has been accomplished, the guiding catheter 786 can be removed.

As soon as the distal extremity of the main catheter 651 has been deployed so that it is just proximal of the stenosis 782 to be treated, an assembly shown in FIG. 33 is introduced into the main catheter 651. This assembly can be provided by preloading the irrigation catheter 766 onto the therapeutic catheter 801 by inserting the distal tip of the therapeutic catheter 801 through the fitting 769 of the irrigation catheter 766 and advancing the therapeutic catheter 801 until its therapeutic balloon 809 exits from the irrigation catheter 766. The balloon-on-a-wire catheter 701 also is preloaded by removing the valve attachment 746 and then inserting the proximal end 703 into the guide wire lumen at the distal tip of the therapeutic catheter 801 and then advanced proximally until the proximal end protrudes out of the proximal end of the therapeutic catheter. The valve attachment 741 is then reattached to the proximal end 703. The preassembled irrigation catheter 766, the therapeutic catheter 801 and the balloon-on-a-wire catheter 701 are then introduced in unison as an assembly into the main catheter 651. The balloon-on-a-wire device 701 is then advanced until the distal extremity is near the distal extremity of the main catheter 651 but before the distal extremity has been advanced through the stenosis 782.

Let it be assumed that it is now desired to inflate the occlusion balloon 669 carried by the main catheter 651. This can be accomplished in a suitable manner such as with an inflation-deflation device represented schematically by a syringe 802 secured to the fitting 687 (see FIG. 33) and supplying a balloon inflation fluid through the balloon inflation lumen 662 to inflate the occlusion balloon 669 to an occlusion pressure ranging from 1 to 3.9 atmospheres and preferably approximately one to two atmospheres to engage the side wall forming the vessel 781 to occlude the vessel 781 and to prevent further blood flow through the vessel and to thereby provide a working space 803 distal of the occlusion balloon 669. As soon as the occlusion balloon 669 has been inflated, the balloon-on-a-wire device 701 can be advanced across the lesion or stenosis 782 until the deflated occlusion balloon 711 carried thereby is distal of the stenosis 782. It is safe to cross the stenosis 782 because the flow of blood through the stenosis 782 has been occluded by the occlusion balloon 669. Thus if any of the plaque forming the stenosis is dislodged by the occlusion balloon 711 on the balloon-on-a-wire device 701 as the occlusion balloon 711 is crossing the stenosis 782, the plaque particles or emboli 804 will not be carried off by blood. The positive pressure of blood in secondary collaterals or vasculature will prevent emboli from traveling downstream into the secondary vasculature. If desired, aspiration can be supplied to the working space 803 encompassing the stenosis 782 by placing a suitable vacuum connected to the fitting 689 of the main catheter.

The occlusion balloon 711 can then be readily inflated by use of a syringe 805 secured to the fitting 751 of the removable valve fitting or attachment 741 of the balloon-on-a-wire device 701 proximal of the fitting 686 and accessible outside the body of the patient. The occlusion balloon 711 is inflated (see FIG. 34) to at least approximately one to two atmospheres to bracket the stenosis and to determine the size of the working space 803 to provide a chamber. It should be appreciated that the size of this working space or chamber 803 can be adjusted by changing the position of the occlusion balloon 711 in the vessel 781. If desired, this can be accomplished while the occlusion balloon 711 is inflated.

Now let it be assumed that the occlusion balloon 711 has been inflated with the appropriate working space 803 and that it is desired to introduce a therapeutic balloon catheter 801 into the working space 803 to treat the stenosis 782. If the therapeutic catheter 801 is not in the main catheter 651 as hereinbefore described, this can be readily accomplished in the present invention by inserting a plug mandrel 756 into the open end of the lumen 706 of the guide wire 702. After the plug mandrel 756 has been inserted, the syringe 805 can be removed after which the thumb screws 748 and 763 can be loosened to permit the o-rings therein to become decompressed and to release the guide wire 702 and the plug mandrel 756 to permit the fitting or valve attachment 741 to be slipped off to provide a proximal end on the guide wire 702 which is free of obstructions. During removal of the valve attachment or fitting 741, the occlusion balloon 711 remains inflated and continues to be disposed distally of the stenosis 782. The occlusion balloon 669 also remains inflated because the syringe 802 remains attached to the fitting 686 and is disposed proximal of the stenosis 782.

The conventional therapeutic catheter 801 then can be delivered over the guide wire 702 if it is not already present. The therapeutic catheter 801 is provided with a flexible elongate tubular member 806 having proximal and distal extremities 807 and 808 with a central flow passage (not shown) extending between the same. A therapeutic balloon 809 on its distal extremity is adapted to be inflated to therapeutic pressures ranging from 4–20 atmospheres through a balloon inflation lumen (not shown) carried by the flexible elongate tubular member 806 through an adapter 811 mounted on the proximal extremity 807. The therapeutic balloon 809 can be considered to be means for performing work carried by the distal extremity 808 of the flexible elongate tubular member 806. The adapter 811 can be removable of the type hereinbefore described or alternatively can be permanently attached thereto. Assuming that it is a removable adapter, the removable adapter 811 is provided with knobs 812 and 813 carrying o-rings (not shown) adapted to establish fluid-tight seals with the flexible elongate member 806 and the plug mandrel 756, respectively. It is also provided with an inflation port 816 similar to those hereinbefore described which is in communication with the inflation lumen (not shown) provided in the flexible elongate tubular member 806 for inflating the therapeutic balloon 809.

After the balloon catheter 801 has been positioned by the use of radiopaque markers (not shown) conventionally employed in such devices, the therapeutic balloon 809 is disposed so that it is in general alignment with the stenosis 782 as shown in FIG. 34. The therapeutic balloon 809 is then inflated in a conventional manner to perform work by use of an inflation-deflation device schematically represented by the syringe 817 attached to the inflation port 816 to the desired pressure to compress the plaque forming the stenosis 782 as shown in FIG. 35 to increase the size of the opening through the stenosis 782 in the vessel 781.

Let it be assumed that during the compression of the plaque forming the stenosis 782, additional emboli 804 are formed as shown in FIG. 36 by pieces of plaque becoming dislodged from the plaque 782 within the vessel 781. Let it also be assumed that it is desired to remove these emboli before deflation of the occlusion balloons 669 and 711 disposed proximally and distally of the stenosis 782. To accomplish this, the therapeutic balloon 809 is deflated by use of the syringe 817. As soon as this has been accomplished, a saline solution can be introduced through the irrigation catheter 766 by connecting a tube 819 carrying the saline solution from a suitable source as for example a free or pressurized saline bag (not shown) and delivered through the irrigation port or side arm 772 where it is carried through the large central lumen of the irrigation catheter 766 so that the saline solution is discharged into the working space 803 disposed between the occlusion balloons 711 and 669 as shown in FIG. 36. At the same time suitable aspiration means is connected to the aspiration port 689 of the adapter 686 and as shown can consist of a hand operated bulb 821 which has a one way check valve 822 therein connected to the fitting 689.

The bulb 821 is provided with another one-way check valve 823 which is connected to a flexible collection bag 824. The bulb 821 makes it possible to generate a vacuum corresponding approximately to 3–30" of mercury. Thus, by compressing the bulb 821 by hand, it is possible to create suction within the chamber or space 803 formed in the vessel between the occlusion balloons 669 and 711 each time the bulb 821 is compressed and released. Alternatively, the aspiration can be accomplished by use of a syringe in place of the bulb 821 and the collection bag 824. Saline liquid supplied through the irrigation catheter 766 carrying is aspirated through the central lumen 657 of the main catheter 651. The aspirated liquid in each cycle of operation created by pressing the bulb 821 is delivered to the collection bag 824. With such a procedure it has been found that it is possible to aspirate emboli as large as 600 μm. Such removal can be assured by observing when clear liquid exits outside the body from the aspiration port 691. A chamber having a length ranging from 3 cm to 15 cm can be totally cleared of emboli within a short period of time ranging from 5 to 30 seconds. Alternatively, irrigation can be accomplished by removing the therapeutic catheter 801 after deflating the therapeutic balloon 809. The irrigation catheter can be advanced over the balloon-on-a-wire device 701 until the distal tip is just proximal of the occlusion balloon 711 as shown in FIG. 37 to provide a greater flow of saline and faster aspiration.

After all of the emboli 804 have been removed, introduction of saline through the tube 819 is halted. It should be appreciated that the ports for irrigation and aspiration can be reversed in function if desired. Thereafter, the occlusion balloon 711 is deflated by removing the plug 756 and utilizing a syringe 805, after which the occlusion balloon 669 is deflated permitting blood flow to be reestablished in the vessel 781. Alternatively, the occlusion balloon 669 can be first deflated and aspiration commenced at that time, permitting emboli trapped distally of the occlusion balloon 669 by blood flowing from the proximal side of the occlusion balloon 669 to be aspirated through the central lumen 657. In order to prevent excessive expansion of the vessel 781 being treated, the pressure of the irrigation liquid is typically maintained under 30 psi. This pressure preferably should be below the occlusion balloon pressure.

If it is desired to deliver a stent to the site of the stenosis formed by the plaque 782, this can be readily accomplished during the same procedure. Typically it is desirable to permit the blood to flow normally for a period of several minutes after which the occlusion balloon 669 can be reinflated by the syringe 805 and the occlusion balloon 711 can be reinflated by inserting the removable valve attachment 741 if it has been removed of the balloon-on-a-wire device 701 and utilizing the syringe 803 to reinflate the occlusion balloon 711. The plug mandrel 756 can be inserted to keep the occlusion balloon 711 inflated after which the valve attachment 741 can be removed.

A conventional stent delivery catheter 826 carrying a stent 827 on its flexible is introduced over the balloon-on-a-wire device 701 and delivered to the site of the dilated stenosis 782 (see FIG. 38). The stent 827 can be of the self-expanding type or of the type which can be expanded by a balloon (not shown) carried by the catheter 826 by connecting a syringe 829 to an adapter 830 of the type hereinbefore described of the stent delivery catheter 826. After the stent 827 has been deployed in the dilated stenosis 782, the stent delivery catheter 826 can be removed after which the occlusion balloon 711 can be deflated followed by deflation of the proximal balloon 661 in the manner hereinbefore described. Also it should be appreciated that if desired in connection with the deployment of the stent delivery catheter 826 before it is removed but after deflation of its balloon (not shown), it may be desirable to again flush the working space or chamber 803 between the occlusion balloons 669 and 711 of emboli which may be dislodged during the delivery and deployment of the stent. The irrigation catheter 766 can be deployed in the same manner as hereinbefore described with a saline irrigation solution supplied to the working space 803 in the manner hereinbefore described and liquid aspirated therefrom by the use of the bulb 821 in the manner hereinbefore described.

Although the foregoing detailed description has described several embodiments of the present invention, it is to be understood that the above description is illustrative only and not limiting of the disclosed invention. It will be appreciated that certain variations of the present invention may suggest themselves to those skilled in the art. Thus, the spirit and scope of this invention are to be limited only by the claims which follow.

What is claimed is:

1. A method of treating a blood vessel, the method comprising:

delivering a first catheter having a lumen in fluid communication with a distal opening in the first catheter into the blood vessel;

delivering a guidewire through the lumen of the first catheter into the blood vessel, the guidewire having a proximal end and a distal end and an occlusive device disposed along the distal end, the occlusive device being actuatable between a nonexpanded state and an expanded state;

delivering a therapy catheter over the guidewire and through the lumen of the first catheter until a distal end of the therapy catheter is proximal to the occlusive device and near a treatment site;

actuating the occlusive device into the expanded state within the vessel at a location distal to a treatment site;

performing therapy on the treatment site using the therapy catheter;

withdrawing the therapy catheter from the blood vessel;

delivering an irrigation catheter over the guidewire until a distal end of the irrigation catheter is proximal to the occlusive device and distal to the distal opening of the first catheter;

supplying irrigation fluid through the irrigation catheter into the blood vessel; and drawing blood and irrigation fluid from the blood vessel into the distal opening of the first catheter while the blood vessel is occluded only by the occlusive device, whereby particles in the blood vessel proximal to the occlusive device are carried by the blood and the irrigation fluid from the vessel into the distal opening and through the lumen of the first catheter.

2. The method of claim 1, wherein the first catheter is a guide catheter.

3. The method of claim 1, wherein the therapy catheter is delivered after actuation of the occlusive device.

4. The method of claim 1, wherein the therapy catheter is delivered before actuation of the occlusive device.

5. The method of claim 1, wherein the therapy catheter is a balloon catheter.

6. The method of claim 1, wherein the therapy catheter deploys a stent.

7. The method of claim 1, wherein the guidewire is hollow.

8. The method of claim 1, wherein the occlusive device is an inflatable balloon.

9. The method of claim 1, wherein the irrigation catheter includes a side member attached along a distal end of the irrigation catheter, the side member defining a side lumen adapted for slidably receiving the guidewire to enable delivery of the irrigation catheter over the guidewire.

10. The method of claim 9, wherein the side member is between about 5 cm and 30 cm in length.

11. The method of claim 9, wherein the side member includes a side wall formed with a longitudinal slit for enabling the guidewire to be inserted into the side lumen through the side wall.

12. The method of claim 1, wherein the irrigation catheter is delivered over the guidewire until the distal end of the irrigation catheter is distal to the treatment site, whereby irrigation fluid flows from the distal end of the irrigation catheter across the treatment site to the distal opening in the first catheter.

* * * * *